US007306922B2

(12) United States Patent
Hart et al.

(10) Patent No.: US 7,306,922 B2
(45) Date of Patent: Dec. 11, 2007

(54) HUMAN AND RAT PGC-3, PPAR-GAMMA COACTIVATIONS AND SPLICE VARIANTS THEREOF

(75) Inventors: Kevin Anthony Hart, Cheshire (GB); Carl Thomas Montague, Cheshire (GB); Antonio Vidal-Puig, Cambridge (GB)

(73) Assignee: AstraZeneca AB, Sodertalje (SE)

( * ) Notice: Subject to any disclaimer, the term of this patent is extended or adjusted under 35 U.S.C. 154(b) by 301 days.

(21) Appl. No.: 10/380,492

(22) PCT Filed: Sep. 12, 2001

(86) PCT No.: PCT/GB01/04074

§ 371 (c)(1),
(2), (4) Date: Mar. 13, 2003

(87) PCT Pub. No.: WO02/22818

PCT Pub. Date: Mar. 21, 2002

(65) Prior Publication Data

US 2004/0077536 A1    Apr. 22, 2004

(30) Foreign Application Priority Data

Sep. 15, 2000    (GB) ................... 0022670.4

(51) Int. Cl.
G01N 33/53    (2006.01)
C07H 21/04    (2006.01)

(52) U.S. Cl. ............... 435/7.1; 536/23.5; 530/350; 435/320.1; 435/325; 435/361; 435/252.3

(58) Field of Classification Search ............ None
See application file for complete search history.

(56) References Cited

U.S. PATENT DOCUMENTS

2002/0048763 A1* 4/2002 Penn et al. ............ 435/6
2003/0171354 A1  9/2003 Wardleworth et al.
2004/0044181 A1* 3/2004 Tang et al. ............ 530/350

FOREIGN PATENT DOCUMENTS

| WO | WO97/21435 A1 | 6/1997 |
|---|---|---|
| WO | WO97/21703 A1 | 6/1997 |
| WO | WO97/21704 A1 | 6/1997 |
| WO | WO97/21707 A1 | 6/1997 |
| WO | WO98/54220 A1 | 12/1998 |
| WO | WO98/55116 A1 | 12/1998 |
| WO | WO98/55119 A1 | 12/1998 |
| WO | WO98/55123 A1 | 12/1998 |
| WO | WO98/55470 A1 | 12/1998 |
| WO | WO98/55479 A1 | 12/1998 |
| WO | WO99/21553 A1 | 5/1999 |
| WO | WO99/21557 A1 | 5/1999 |
| WO | WO99/41251 A1 | 8/1999 |
| WO | WO99/41252 A1 | 8/1999 |
| WO | WO99/51231 A1 | 10/1999 |
| WO | WO99/51232 A1 | 10/1999 |
| WO | WO99/51233 A1 | 10/1999 |
| WO | WO99/51234 A1 | 10/1999 |
| WO | WO99/51595 A1 | 10/1999 |
| WO | WO99/51596 A1 | 10/1999 |
| WO | WO 00/04013 A1 | 1/2000 |
| WO | WO 00/32215 A1 | 6/2000 |
| WO | WO 00/53178 A1 | 9/2000 |
| WO | WO 00/53179 A1 | 9/2000 |
| WO | WO 00/53180 A1 | 9/2000 |
| WO | WO 00/53181 A1 | 9/2000 |
| WO | WO 00/53185 A1 | 9/2000 |
| WO | WO 00/53602 A1 | 9/2000 |
| WO | WO 00/69433 A1 | 11/2000 |
| WO | WO 01/57272 A2 | 8/2001 |
| WO | WO 01/57275 A2 | 8/2001 |
| WO | WO-02/18424 A2 | 3/2002 |

OTHER PUBLICATIONS

Esterbauer et al., Genomics (1999), vol. 62, pp. 98-102.*
Lin et al., The Journal of Biological Chemistry, vol. 277, No. 3, Jan. 18, 2002, pp. 1645-1648.*
Meirhaghe et al., Biochemical Journal, vol. 373, 2003, pp. 155-165.*
P. Puigserver et al., "A cold-inducible coactivator of nuclear receptors linked to adaptative thermogenesis." Cell, vol. 92, Mar. 20, 1998.
Database EMBL 'Online! Accession No. AW236547, Dec. 15, 1999 "xm47f06.x1 NCI_CGAP_GC6 homo sapiens cDNA clone IMAGE:2687363 3' similar to TR:070343 PPAR Gamma Coactivator 1" XP002188800.
Database EMBL 'Online! Accession No. AW149754, Nov. 4, 1999 "xf41h08.x1 NCI_CGAP_Brn50 homo sapiens cDNA clone IMAGE:2620671 3' similar to TR:070343 PPAR Gamma Coactivator 1" XP002188801.
Esterbauer et al, "Human Peroxisome Proliferator Activated Receptor Gamma Coactivator 1 (PPARGC1) Gene: cDNA Sequence, Genomic Organization, Chromosomal Localization, and Tissue Expression." Genomics (1999), vol. 62, pp. 98-102.
Larrouy et al., "Cloning and mRNA tissue distribution of huma PPARγ coactivator 1." International Journal of Obesity (1999), vol. 23, pp. 1327-1332.
Knutti et al., "A Tissue-Specific Coactivator of Steroid Receptors, Identified in a Functional Genetic Screen." Mol. Cell Biol. (2000), vol. 20(7), pp. 2411-2422.

(Continued)

Primary Examiner—Eileen B. O'Hara
(74) Attorney, Agent, or Firm—Ropes & Gray LLP

(57) ABSTRACT

A novel gene PGC-3, and its role in regulating the transcriptional activity of PPARγ in adipose tissue. PGC-3 is highly expressed in human white adipose tissue and has utility in the development of new therapeutic agents for use in the treatment of obesity and other related disorders such as non-insulin dependent diabetes mellitus, insulin resistance syndrome, dyslipidemia, and atherosclerosis.

13 Claims, 4 Drawing Sheets

OTHER PUBLICATIONS

Ashton, W. et al, Substituted Indole-5-carboxamides and -acetamides as Potent Nonpeptide GnRH Receptor Antagonists, Bioorganic & Medicinal Chemistry Letters 11: 1723-1726 (2001).

Ashton, W. et al, Potent Nonpeptide GnRH Receptor Antagonists Derived from Substituted Indole-5-carboxamides and -acetamides Bearing a Pyridine Side-Chain Terminus, Bioorganic & Medicinal Chemistry Letters 11: 1727-1731 (2001).

Ashton, W. et al, Orally Bioavailable, Indole-Based Nonpeptide GnRH Receptor Antagonists with High Potency and Functional Activity, Bioorganic & Medicinal Chemistry Letters 11: 2597-2602 (2001).

Chu, L. et al, SAR Studies of Novel 5-Substituted 2-Arylindoles as Nonpeptidyl GnRH Receptor Antagonists, Bioorganic & Medicinal Chemistry Letters 11: 515-517 (2001).

Chu, L. et al, Initial Structure-Activity Relationship of a Novel Class of Nonpeptidyl GnRH Receptor Antagonists: 2-Arylindoles, Bioorganic & Medicinal Chemistry Letters 11: 509-513 (2001).

Freidinger, R., Nonpeptidic ligands for peptide and protein receptors, Current Opinion in Chemical Biology 3: 395-406 (1999).

Lin, P. et al, Heterocyclic Derivatives of 2-(3,5-Dimethylphenyl) tryptamine as GnRH Receptor Antagonists, Bioorganic & Medicinal Chemistry Letters 11: 1077-1080 (2001).

Lin, P. et al, 2-(3,5-Dimethylphenyl) tryptamine Derivatives That Bind to the GnRH Receptor, Bioorganic & Medicinal Chemistry Letters 11: 1073-1076 (2001).

Goulet, M., Gonadotropin Releasing Hormone Antagonists, Annual Reports in Medicinal Chemistry 30: 169-178 (1995).

Simeone, J. et al, Synthesis of chiral β-methyl tryptamine-derived GnRH antagonists, Tetrahedron Letters 42: 6459-6461 (2001).

Ujjainwalla, F. et al, Total syntheses of 6- and 7-azaindole derived GnRH antagonists, Tetrahedron Letters 42: 6441-6445 (2001).

Walsh, T. et al, A convergent synthesis of (S)-β-methyl-2-aryltryptamine based gonadotropin releasing hormone antagonists, Tetrahedron 57: 5233-5241 (2001).

Young, J. et al, 2-Arylindoles as Gonadotropin Releasing Hormone (GnRH) Antagonists: Optimization of the Tryptamine Side Chain, Bioorganic & Medicinal Chemistry Letters 12: 827-832 (2002).

* cited by examiner

```
Human  -MGVYKGGGSGEEQLYADFPELDLSQLDASDFDSATCFGELQWCPENSETEPNQYSPDDS
        * *** ****** **:****************************.*****.******
Rat    MQGEGKGGESGEEQLCADLPELDLSQLDASDFDSATCFGELQWCPETSETEPSQYSPDDS Human  ELFQIDSENEALLAELTKTLDDIPEDDVGLAAFPALDGGDALSCTSASPAPSSAPPSPAP
       *:************.************. : *.***** *.*****
Rat    EFFQIDSENEALLAALTKTLDDIPEDDVGLAAFPGLDEGDTPSCTPASPAPLSVPPSPAL Human  EKPSAPAPEVDELSLLQKLLLATSYPTSSSDTQKEGTAWRQAGLRSKSQRPCVKADSTQD
       *: :*..********** :***: *;*::* *:.* *:*******.*.***
Rat    ERLLSPVSEVDELSLLQKLLLATSSPTASSDALKDGATWSQTSLSSRSQRPCVKVDGTQD Human  KKAPMMQSQSRSCTELHKHLTSAQCCLQDRGLQPPCLQSPRLPAKEDKEPGEDCPSPQPA
       ::;**.********.  *  ;.:. .   :* ;***:* *****.
Rat    KKTPMLRSQSRPCTELHKHLTSVLPCPRGKACSPPPHPSPQLLSKEDEEVGEDCPSPWPA Human  PASPQDSLALGRADPG-APVSQEDMQAMVQLIRYMHTYCLPQRKLPPQTPEPLPKACSNP
       ********.  .*;*. * *.::*::******************  ::.:*:;**.*
Rat    PASPQDSLGQDTANPNSAQVPKDDVRAMVQLIRYMHTYCLPQRKLPQRASEPIPQSCSSP Human  SQQVRSRPWSRHHSKASWAEFSILRELLAQDVLCDVSKPYRLATPVYASLTPRSRPRPPK
       ::*    * : . *:.********:**************;.****
Rat    LRKVP--PRSRQTPKAFWTEFSILRELLAQDILCDVSKPYRLATPVYASLTPQSRTRPPK Human  DSQASPGRPSSVEEVRIAASPKSTGPRPSLRPLRLEVKREVRRPARLQQQEEEDEEEEEE
       ****.;..: .*.*****************.*.;*** ;::*;*;******
Rat    DSQASPAHSAMAEEVRITASPKSTGPRPSLRPLRLEVKRDVNKPARQKREEDEEEEEEEE Human  EEEEEKEEEEEWGRKRPGRGLPWTKLGRKLESSVCPVRRSRRLNPELGPWLTFADEPLVP
       **:::***********************:;****************;**
Rat    EEEEKEDEEEEWGRKRPGRGLPWTKLGRKMDSSVCPVRRSRRLNPELGPWLTFTDEPLG- Human  SEPQGALPSLCLAPKAYDVERELGSPTDEDSGQDQQLLRGPQIPALESPCESGCGDMDED
            **;*.;::*;*.*.  *.*.*** *.*:******** *
Rat    -----ALPSMCLATETHDLEEELGGLTD--SSQGQQLPLGSQIPTLESPCESGCGDTDED Human  PSCPQLPPRDSPRCLMLALSQSDPTFGKKSFEQTLTVELCGTAGLTPPTTPPYKPTEEDP
       ****: *.************ ;**::****************.**
Rat    PSCPRPPSRDSPRCLMLALSQSDP-LGKKSFEESLTVELCGTAGLTPPTTPPYKPMEEDP
```

FIGURE 3

```
Human   FKPDIKHSLGKEIALSLPSPEGLSLKATPGAAHKLPKKHPERSELLSHLRHATAQPASQA
        ** * *** *:: * ****** *.*.*****:*****:************:***:**.***
Rat     FKQDTKHSPGQDTAPSLPSPETLQLTATPGASHKLPKRHPERSELLSHLQHATTQPVSQA Human   GQKRPFSCSFGDHDYCQVLRPEGVLQRKVLRSWEPSGVHLEDWPQQGAPW-AEAQAPGRE
        ***************:*..********* *  .:*.  .*:::* **
Rat     GQKRPFSCSFGDHDYCQVIRPEAALQRKVLRSWEPIKVHLEDLAHQGATLPVETKTPRRE Human   EDRSCDAGAPPKDSTLLRDHEIRASLTKHFGLLETALEEEDLASCKSPEYDTVFEDSSSS
        *:..  .  *******************************************
Rat     ADQNCDP--TPKDSMQLRDHEIRASLTKHFGLLETALEEEDLASCKSPEYDTVFEDSSSS Human   SGESSFLPEEEEEEGEEEEEDDEEEDSGVSPTCSDHCPYQSPPSKANRQLCSRSRSSSGS
        ***** **   * **.********** ***********
Rat     SGESSFLLEEEEEEGGEE--DDEGEDSGVSPPCSDHCPYQSPPSKASRQLCSRSRSSSGS Human   SPCHSWSPATRRNFRCESRGPCSDRTPSIRHARKRREKAIGEGRVVYIQNLSSDMSSREL
        *.* *****:* ****** * *:*********:*_*******
Rat     SSCSSWSPATRKNFRLESRGPCSDGTPSARHAKKRREKAIGEGRVVYIRNLSGDMSSREL Human   KRRFEVFGEIEECEVLTRNRRGEKYGFITYRCSEHAALSLTKGAALRKRNEPSFQLSYGG
        *:****** :** *_:**:*:**:*****:  ::*******:***
Rat     KKRFEVFGEIVECQVLRRSKRGQKHGFITFRCSEHAALSVRNGATLRKRNEPSFHLSYGG Human   LRHFCWPRYTDYDSNSEEALPASGKSKYEAMDFDSLLKEAQQSLH
        ** ****_.*::********************
Rat     LRHFRWPRYTDYDPTSEESLPSSGKSKYEAMDFDSLLKEAQQSLH
```

FIGURE 3 continued

HUMAN AND RAT PGC-3, PPAR-GAMMA COACTIVATIONS AND SPLICE VARIANTS THEREOF

This application is a national stage filing under 35 U.S.C. 371 of International Application No. PCT/GB01/04074, filed Sep. 12, 2001, which claims priority from United Kingdom Application No. 0022670.4, filed Sep. 15, 2000, the specifications of each of which are incorporated by reference herein. International Application No. PCT/GB01/04074 was published under PCT Article 21(2) in English.

This invention relates to the regulation of metabolism and in particular to human genes involved in obesity. The invention further relates to proteins encoded by the genes and to means of regulating their biological activity. In addition the invention relates to the use of the genes and proteins to identify therapeutic agents for controlling obesity and other related disorders such as non-insulin dependent diabetes mellitus (NIDDM), insulin resistance syndrome, dyslipidemia, and atherosclerosis.

Obesity results from an excessive accumulation of adipose tissue and is a growing public health problem in developed and developing countries. Highly overweight individuals show significant increases in the occurrence of NIDDM, coronary heart disease, some cancers and digestive diseases.

Current treatment is unsatisfactory and new drugs need to be developed. A major problem is that the mechanisms regulating obesity, and the role of increased adiposity in the development of metabolic dysfunction are unclear. What is apparent is that obesity results from an imbalance between energy intake and expenditure. Energy expenditure can be affected by alterations in basal metabolism, physical activity and adaptive thermogenesis.

Peroxisome proliferator-activated receptor-γ (PPARγ) is a recently identified member of the peroxisome proliferator-activated receptor family of nuclear hormone receptors (Tontonoz et al., Genes Dev. (1994) 8, 1224–1234). The expression of this protein is induced very early in the adipocyte differentiation process and, when expressed ectopically in fibroblastic cells, induces adipogenesis in response to activators of the receptor. Synthetic and naturally occurring ligands for PPARγ have been identified. Thiazolidinediones (TZDs), a class of insulin sensitising agents which are used for the treatment of NIDDM, have been shown to bind to and activate PPARγ. TZDs promote adipocyte differentiation of murine and human preadipocytes to mature, fat storing adipocytes. TZD activation of PPARγ has also been shown to regulate transcription of many adipocyte genes. In addition to the presence of a ligand, the activity of PPARγ has been shown to be influenced by the presence of coactivators and corepressors. When co-expressed in cells alongside PPARγ these proteins have been shown to greatly increase or repress the transcriptional activity of PPARγ. Differences in expression of these coactivators and corepressors between cell types may explain the observed differences in PPARγ mediated transcriptional activity between cells from different tissues.

One such coactivator is PGC-1 (Puigserver et al., Cell (1998) 92, 829–839). The expression of this 90 kDa nuclear protein is greatly increased in muscle and brown fat of mice upon their exposure to cold temperatures. Co-expression of PGC-1 with PPARγ has been shown to activate aspects of the adaptive thermogenic program.

However, PGC-1 is not expressed in white adipose tissue which makes up the majority of adipose tissue found in humans. The identification of a protein which regulates the activity of PPARγ in white adipose tissue is thus of great importance in understanding the development of human obesity.

In the present invention we disclose the cloning and identification of PGC-3, and its role in regulating the transcriptional activity of PPARγ in adipose tissue. PGC-3 is highly expressed in human white adipose tissue and shares sequence homology with PGC-1 in domains known to be responsible for distinct activity of the protein. Two distinct variants of PGC-3 have been identified, termed PGC-3a and PGC-3b, which arise from alternative splicing of the PGC-3 gene. A further splice variant has been identified, termed PGC-3c. Full length cDNA and protein sequences for each of the splice variants are provided. The invention further discloses that PGC-3 has utility in the development of new therapeutic agents for use in the treatment of obesity and other related disorders such as non-insulin dependent diabetes mellitus, insulin resistance syndrome, dyslipidemia, and atherosclerosis. The invention further provides methods for the identification of such therapeutic agents.

Unless defined otherwise, all technical and scientific terms used herein have the same meaning as is commonly understood by one of skill in the art to which this invention belongs. All publications and patents referred to herein are incorporated by reference.

The term "PGC-3" as used herein encompasses both of the splice variants, PGC-3a and PGC-3b, as well as PGC-3c.

According to one aspect of the present invention we provide an isolated and purified polynucleotide molecule comprising a nucleic acid sequence which encodes a polypeptide having at least about 90% homology to a member selected from any one of (a) (SEQ ID NO:2, SEQ ID NO:2 positions 1–600, SEQ ID NO:2 positions 400–1002, and SEQ ID NO:2 positions 200–800)

or (b) (SEQ ID NO:4, SEQ ID NO:4 positions 1–600, SEQ ID NO:4 positions 400–996, and SEQ ID NO:4 positions 200–800)

or (c) (SEQ ID NO: 8, SEQ ID NO: 8 positions 1–600, SEQ ID NO: 8 positions 400–1023, and SEQ ID NO: 8 positions 200–800).

Isolated and purified polynucleotides of the present invention include sequences which comprise the human PGC-3a cDNA sequence set out in SEQ ID NO:1 and the human PGC-3b cDNA sequence set out in SEQ ID NO:3 and the human PGC-3c cDNA sequence set out in SEQ ID NO:7.

In addition we have also identified and sequenced a rat clone having a high degree of homology to PGC-3 (cf. Example 5). Polynucleotide and polypeptide molecules based on the rat PGC-3 sequence may be used by analogy with the human sequences. The rat sequence shows a high degree of sequence homology (78% sequence identity and rats are therefore expected to be useful in animal models of metabolism.

Therefore in a further aspect of the invention we provide an isolated and purified polynucleotide molecule comprising a nucleic acid sequence which encodes a polypeptide having at least about 90% homology to any one of SEQ ID NO:10, SEQ ID NO:10 positions 1–600, SEQ ID NO: 10 positions 400–990, and SEQ ID NO:10 positions 200–800.

In a further aspect of the invention we provide fragments of the isolated and purified polynucleotide molecules of the present invention. By fragments we mean contiguous regions of the polynucleotide molecule including complementary DNA and RNA sequences, starting with short sequences useful as probes or primers of say about 8–50 bases, such as 10–30 bases or 15–35 bases, to longer sequences of up to 50, 100, 200, 500 or 1000 bases. Indeed any convenient fragment of the polynucleotide molecule may be a useful fragment for further research, therapeutic or diagnostic purposes. Further convenient fragments include those whose terminii are defined by restriction sites within the molecule of one or more kinds, such as any combination of Rsa1, Alu1 and Hinf1.

In a further aspect we provide homologues and orthologues of the isolated and purified polynucleotide molecules of the present invention. Preferred homologues and orthologues are polynucleotide molecules which display greater than 80% sequence homology, conveniently greater than 85%, for example 90%, to the PGC-3 cDNA sequences set out in SEQ ID NO:1 and SEQ ID NO:3. A homologue may be a polynucleotide molecule from the same species i.e. a homologous family member, alternatively, the homologue may be a similar polynucleotide molecule from a different species such as human, useful in developing new therapies for the treatment of IRS and other related disorders such as NIDDM, obesity and atherosclerosis. By the term orthologue we mean a functionally equivalent molecule in another species. The full sequences of the individual homologues and orthologues may be determined using conventional techniques such as hybridisation, PCR and sequencing techniques, starting with any convenient part of the sequence set out in SEQ ID NO: 1 or SEQ ID NO:3.

In a further aspect of the invention we provide isolated and purified polynucleotide molecules capable of specifically hybridising to the polynucleotide molecules of the present invention. By specifically hybridising we mean that the polynucleotide hybridises by base-pair interactions, under stringent conditions, to the polynucleotide molecules of the present invention or to the corresponding complementary sequences. Experimental procedures for hybridisation under stringent conditions are well known to persons skilled in the art. For example, hybridisation filters may be incubated overnight at 42° C. in a solution comprising 50% formamide, 5×SSC (150 mM NaCl, 15 mM trisodium citrate), 50 mM sodium phosphate (pH7.6) 5× Denhardt's solution, 10% dextran sulphate, and 20 µg/ml denatured salmon sperm DNA; followed by washing the filters in 0.1×SSC at about 65° C. Hybridisation techniques are thoroughly described in Sambrook J., Fritsch E. F. and Maniatis T., Molecular Cloning a Laboratory Manual, Cold Spring Harbor Laboratory Press, 1989.

In a further aspect we provide an expression vector comprising a polynucleotide molecule of the present invention.

A variety of mammalian expression vectors may be used to express the recombinant polypeptides of the present invention. Commercially available mammalian expression vectors which are suitable for recombinant expression include, pcDNA3 (Invitrogen), pMC1neo (Stratagene), pXT1 (Stratagene), pSG5 (Stratagene), EBO-pSV2-neo (ATCC 37593), pBPV-1(8-2) (ATCC 37110), pdBPV-MMT-neo (342-12) (ATCC 37224), pRSVgpt (ATCC 37199), pRSVneo (ATCC 37198), pSV2-dhfr (ATCC 37146), pUC-Tag (ATCC 37460), IZD35 (ATCC 37565), pLXIN, pSIR (CLONTECH), and pIRES-EGFP (CLONTECH).

Baculoviral expression systems may also be used with the present invention to produce high yields of biologically active polypeptides. Preferred vectors include the CLONTECH, BacPak™ Baculovirus expression system and protocols which are commercially available (CLONTECH, Palo Alto, Calif.).

Further preferred vectors include vectors for use with the mouse erythroleukemia cell (MEL cell) expression system comprising the human beta globin gene locus control region (Davies et al., J. of Pharmacol. and Toxicol. Methods 33, 153–158).

Vectors comprising one or more polynucleotide molecules of the present invention may then be purified and introduced into appropriate host cells. Therefore in a further aspect we provide a transformed host cell comprising a polynucleotide molecule of the present invention.

The polypeptides of the present invention may be expressed in a variety of hosts such as bacteria, plant cells, insect cells, fungal cells and human and animal cells. Eukaryotic recombinant host cells are especially preferred. Examples include yeast, mammalian cells including cell lines of human, bovine, porcine, monkey and rodent origin, and insect cells including *Drosophila* and silkworm derived cell lines. Cell lines derived from mammalian species which may be used and which are commercially available include, L cells L-M(TK-) (ATCC CCL 1.3), L cells L-M (ATCC CCL 1.2), HEK 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells to express a polypeptide of the present invention via any one of a number of techniques including calcium phosphate transformation, DEAE-dextran transformation, cationic lipid mediated lipofection, electroporation or infection The transformed host cells are propagated and cloned, for example by limiting dilution, and analysed to determine the expression level of recombinant polypeptide. Identification of transformed host cells which express a polypeptide of the present invention may be achieved by several means including immunological reactivity with antibodies described herein and/or the detection of biological activity.

Polypeptides of the present invention may be expressed as fusion proteins, for example with one or more additional polypeptide domains added to facilitate protein purification. Examples of such additional polypeptides include metal chelating peptides such as histidine-tryptophan modules that allow purification on immobilised metals (Porath, J., Protein Exp. Purif. 3:263 (1992)), protein A domains that allow purification on immobilised immunoglobulin, and the domain utilised in the FLAGS extension/affinity purification system (Immunex Corp, Seattle Wash.). The inclusion of cleavable linker sequences such as Factor XA or enterokinase (Invitrogen, San Diego Calif.) between the purification domain and the coding region is useful to facilitate purification. A preferred protein purification system is the CLONTECH, TALON™ nondenaturing protein purification kit for purifying 6× His-tagged proteins under native conditions (CLONTECH, Palo Alto, Calif.).

Therefore in a further aspect we provide a method for producing a polypeptide of the present invention, which method comprises culturing a transformed host cell comprising a polynucleotide of the present invention under conditions suitable for the expression of said polypeptide.

In a further aspect of the present invention we provide a purified polypeptide comprising the human PGC-3a amino acid sequence set out in SEQ ID NO:2 or a variant of SEQ ID NO:2 having at least about 90% homology to a member selected from (SEQ ID NO:2 positions 1–600, SEQ ID NO:2 positions 400–1002, SEQ ID NO:2 positions 200–800), or a biologically active fragment thereof.

In a further aspect of the present invention we provide a purified polypeptide comprising the human PGC-3b amino acid sequence set out in SEQ ID NO:4 or a variant of SEQ ID NO:4 having at least about 90% homology to a member selected from (SEQ ID NO:4 positions 1–600, SEQ ID NO:4 positions 400–996, SEQ ID NO:4 positions 200–800), or a biologically active fragment thereof.

In a further aspect of the present invention we provide a purified polypeptide comprising the human PGC-3c amino acid sequence set out in SEQ ID NO:8 or a variant of SEQ ID NO:8 having at least about 90% homology to a member selected from (SEQ ID NO:8 positions 1–600, SEQ ID NO:8 positions 400–1023, SEQ ID NO:8 positions 200–800), or a biologically active fragment thereof.

In a further aspect of the present invention we provide a purified polypeptide comprising the rat PGC-3 amino acid sequence set out in SEQ ID NO:10 or a variant of SEQ ID NO:10 having at least about 90% homology to a member selected from (SEQ ID NO:10 positions 1–600, SEQ ID NO:10 positions 400–990, SEQ ID NO:10 positions 200–800), or a biologically active fragment thereof.

A variant is a polynucleotide or polypeptide which differs from a reference polynucleotide or polypeptide, but which retains some of its essential characteristics. For example, a variant of a PGC-3 polypeptide may have an amino acid sequence that is different by one or more amino acid substitutions, deletions and/or additions. The variant may have conservative changes (amino acid similarity), wherein a substituted amino acid has similar structural or chemical properties, for example, the replacement of leucine with isoleucine. Alternatively, a variant may have nonconservative changes, e.g., replacement of a glycine with a tryptophan. Guidance in determining which and how many amino acid residues may be substituted, inserted or deleted and the effect this will have on biological activity may be reasonably inferred from the present disclosure by a person skilled in the art and may further be found using computer programs well known in the art, for example, DNAStar software.

Amino acid substitutions may be made, for instance, on the basis of similarity in polarity, charge, solubility, hydrophobicity, hydrophilicity, and/or the amphipathic nature of the residues. Negatively charged amino acids, for example, include aspartic acid and glutamic acid; positively charged amino acids include lysine and arginine; and amino acids with uncharged polar head groups having similar hydrophilicity values include leucine, isoleucine, valine, glycine, alanine; asparagine, glutamine; serine, threonine, phenylalanine, and tyrosine.

Suitable substitutions of amino acids include the use of a chemically derivatised residue in place of a non-derivatised residue. D-isomers and other known derivatives may also be substituted for the naturally occurring amino acids. See, e.g., U.S. Pat. No. 5,652,369, Amino Acid Derivatives, issued Jul. 29, 1997. Example substitutions are set forth in Table 1.

"Homology" as used in this description is a measure of the similarity or identity of nucleotide sequences or amino acid sequences. In order to characterise the homology, subject sequences are aligned so that the highest order identity match is obtained. Identity can be calculated using published techniques. Computer program methods to determine identity between two sequences, for example, include DNAStar software (DNAStar Inc., Madison, Wis.); the GCG program package (Devereux, J., et al., Nucleic Acids Research 1984, 12(1):387); and BLASTP, BLASTN, FASTA (Atschul, S. F. et al., J Molec Biol 1990, 215:403). Homology as defined herein is determined conventionally using the well known computer program, BESTFIT (Wisconsin Sequence Analysis Package, Version 8 for Unix, Genetics Computer Group, University Research Park, 575 Science Drive, Madison, Wis., 53711). When using BESTFIT or another sequence alignment program to determine the similarity of a particular sequence to a reference sequence, the parameters are typically set such that the percentage identity is calculated over the full length of the reference nucleotide sequence or amino acid sequence and that gaps in homology of up to about 10% of the total number of nucleotides or amino acid residues in the reference sequence are allowed.

In a further aspect we provide polymorphic variants of the polynucleotides and polypeptides of the present invention. Polymorphisms are variations in polynucleotide or polypeptide sequences between one individual and another. DNA polymorphisms may lead to variations in amino acid sequence and consequently to altered protein structure and functional activity. Polymorphisms may also affect mRNA synthesis, maturation, transport and stability. Polymorphisms which do not result in amino acid changes (silent polymorphisms) or which do not alter any known consensus sequences may nevertheless have a biological effect, for example by altering mRNA folding or stability.

Knowledge of polymorphisms may be used to help identify patients most suited to therapy with particular pharmaceutical agents (this is often termed "pharmacogenetics"). Pharmacogenetics may also be used in pharmaceutical research to assist the drug selection process. Polymorphisms may be used in mapping the human genome and to elucidate the genetic component of diseases. The reader is directed to the following references for background details on pharmacogenetics and other uses of polymorphism detection: Linder et al. (1997), Clinical Chemistry, 43, 254; Marshall (1997), Nature Biotechnology, 15, 1249; International Patent Application WO 97/40462, Spectra Biomedical; and Schafer et al. (1998), Nature Biotechnology, 16, 33.

The polypeptides of the present invention may be genetically engineered in such a way that their interaction with other intracellular and membrane associated proteins are maintained but their effector function and biological activity are removed. A polypeptide genetically modified in this way is known as a dominant negative mutant. In the construction of a dominant negative mutant at least one amino acid residue position at a site required for activity in the native peptide is changed to produce a peptide which has reduced activity or which is devoid of detectable activity. Overexpression of the dominant negative mutant in an appropriate cell type down-regulates the effect of the endogenous polypeptide, thereby revealing the biological mechanisms involved in the control of metabolism.

Similarly, the polypeptides of the present invention may be genetically engineered in such a way that their effector function and biological activity are enhanced. The resultant overactive polypeptide is known as a dominant positive mutant. At least one amino acid residue position at a site required for activity in the native peptide is changed to produce a peptide which has enhanced activity. Overexpression of a dominant positive mutant in an appropriate cell type amplifies the response of the endogenous native polypeptide highlighting the regulatory mechanisms controlling cell metabolism.

Therefore in a further aspect we provide dominant negative and dominant positive mutants of the polypeptides of the present invention.

Novel sequences disclosed herein, may be used in another embodiment of the invention to regulate expression of PGC-3 genes in cells by the use of antisense constructs. For example an antisense expression construct may be readily constructed using the pREP10 vector (Invitrogen Corporation). Transcripts are expected to modulate translation of the gene in cells transfected with the construct. Antisense transcripts are effective for modulating translation of the native gene transcript, and are capable of altering the effects (e.g., regulation of tissue physiology) herein described. Oligonucleotides which are complementary to and hybridisable with any portion of mRNA disclosed herein are contemplated for therapeutic use. U.S. Pat. No. 5,639,595, "Identification of Novel Drugs and Reagents", issued Jun. 17, 1997, wherein methods of identifying oligonucleotide sequences that display in vivo activity are thoroughly described, is herein incorporated by reference. Antisense molecules may also be synthesised for use in antisense therapy, using techniques known to persons skilled in the art. These antisense molecules may be DNA, stable derivatives of DNA such as phosphorothioates or methylphosphonates, RNA, stable derivatives of RNA such as 2'-O-alkylRNA, or other oligonucleotide mimetics. U.S. Pat. No. 5,652,355, "Hybrid Oligonucleotide Phosphorothioates", issued Jul. 29, 1997, and U.S. Pat. No. 5,652,356, "Inverted Chimeric and Hybrid Oligonucleotides", issued Jul. 29, 1997, which describe the synthesis and effect of physiologically-stable antisense molecules, are incorporated by reference. Antisense molecules may be introduced into cells by microinjection, liposome encapsulation or by expression from vectors harboring the antisense sequence.

In a further aspect we provide an antibody specific for a polypeptide of the present invention.

Antibodies can be prepared using any suitable method, for example, purified polypeptide may be utilised to prepare specific antibodies. The term "antibodies" includes polyclonal antibodies, monoclonal antibodies, and the various types of antibody constructs such as for example F(ab')$_2$, Fab and single chain Fv. Antibodies are defined to be specifically binding if they bind the antigen with a $K_a$ of greater than or equal to about $10^7 M^{-1}$. Affinity of binding can be determined using conventional techniques, for example those described by Scatchard et al., *Ann. N.Y. Acad. Sci.*, 51:660 (1949).

Polyclonal antibodies can be readily generated from a variety of sources, for example, horses, cows, goats, sheep, dogs, chickens, rabbits, mice or rats, using procedures that are well-known in the art. In general, antigen is administered to the host animal typically through parenteral injection. The immunogenicity of antigen may be enhanced through the use of an adjuvant, for example, Freund's complete or incomplete adjuvant. Following booster immunisations, small samples of serum are collected and tested for reactivity to antigen. Examples of various assays useful for such determination include those described in: *Antibodies: A Laboratory Manual*, Harlow and Lane (eds.), Cold Spring Harbor Laboratory Press, 1988; as well as procedures such as countercurrent immuno-electrophoresis (CIEP), radioimmunoassay, radioimmunoprecipitation, enzyme-linked immuno-sorbent assays (ELISA), dot blot assays, and sandwich assays, see U.S. Pat. Nos. 4,376,110 and 4,486,530.

Monoclonal antibodies may be readily prepared using well-known procedures, see for example, the procedures described in U.S. Pat. Nos. RE 32,011, 4,902,614, 4,543,439 and 4,411,993; Monoclonal Antibodies, Hybridomas: A New Dimension in Biological Analyses, Plenum Press, Kennett, McKearn, and Bechtol (eds.), (1980).

The monoclonal antibodies of the invention can be produced using alternative techniques, such as those described by Alting-Mees et al., "Monoclonal Antibody Expression Libraries: A Rapid Alternative to Hybridomas", *Strategies in Molecular Biology* 3: 1–9 (1990) which is incorporated herein by reference. Similarly, binding partners can be constructed using recombinant DNA techniques to incorporate the variable regions of a gene that encodes a specific binding antibody. Such a technique is described in Larrick et al., *Biotechnology*, 7: 394 (1989).

Once isolated and purified, the antibodies may be used to detect the presence of antigen in a sample using established assay protocols.

In a further aspect of the invention we provide a method for identifying a therapeutic agent capable of modulating the activity of PGC-3 for use in the regulation of metabolism, which method comprises:

(i) contacting a candidate compound modulator with a PGC-3 polypeptide comprising any one of (a) the amino acid sequence set out in SEQ ID NO:2 or a variant of SEQ ID NO:2 having at least about 90% homology to a member selected from (SEQ ID NO:2 positions 1–600, SEQ ID NO:2 positions 400–1002, SEQ ID NO:2 positions 200–800) or a biologically active fragment thereof;

or (b) the amino acid sequence set out in SEQ ID NO:4 or a variant of SEQ ID NO:4 having at least about 90% homology to a member selected from (SEQ ID NO:4 positions 1–600, SEQ ID NO:4 positions 400–996, SEQ ID NO:4 positions 200–800) or a biologically active fragment thereof;

or (c) the amino acid sequence set out in SEQ ID NO:8 or a variant of SEQ ID NO:8 having at least about 90% homology to a member selected from (SEQ ID NO:8 positions 1–600, SEQ ID NO:8 positions 400–996, SEQ ID NO:8 positions 200–800) or a biologically active fragment thereof;

and (ii) measuring an effect of the candidate compound modulator on the activity of the PGC-3 polypeptide.

Activity as used herein refers to the ability of the therapeutic agent to mediate cell processes related to insulin resistance syndrome and other related disorders such as non-insulin dependent diabetes mellitus, dyslipidemia, obesity and atherosclerosis.

Modulation of the activity of PGC-3 comprises either stimulation or inhibition. Thus a therapeutic agent capable of modulating the activity of PGC-3 is an agent that either stimulates or inhibits the activity of PGC-3. The terms "modulator of PGC-3 activity" and "PGC-3 modulator" are also used herein to refer to an agent that either stimulates or inhibits the activity of PGC-3. The therapeutic agents of the invention have utility in the regulation of metabolism; in particular in obesity and the control of insulin resistance syndrome and other related disorders such as non-insulin dependent diabetes mellitus, dyslipidemia, and atherosclerosis.

In a further aspect of the invention we provide a screen for identifying compounds which modulate the activity of PGC-3, the invention extends to such a screen and to the use of compounds obtainable therefrom to modulate the activity of PGC-3 in vivo.

Potential therapeutic agents which may be tested in the screen include simple organic molecules, commonly known as "small molecules", for example those having a molecular weight of less than 2000 Daltons. The screen may also be used to screen compound libraries such as peptide libraries, including synthetic peptide libraries and peptide phage libraries. Other suitable molecules include antibodies, nucleotide sequences and any other molecules which modulate the activity of PGC-3.

Once an inhibitor or stimulator of PGC-3 activity is identified then medicinal chemistry techniques can be applied to further refine its properties, for example to enhance efficacy and/or reduce side effects.

It will be appreciated that there are many screening procedures which may be employed to perform the present invention. Examples of suitable screening procedures which may be used to identify a PGC-3 modulator for use in the regulation of metabolism include rapid filtration of equilibrium binding mixtures, enzyme linked immunosorbent assays (ELISA), radioimmunoassays (RIA) and fluorescence resonance energy transfer assays (FRET). For further information on FRET the reader is directed to International Patent Application WO 94/28166 (Zeneca). Methods to identify potential drug candidates have been reviewed by Bevan P et al., 1995, TIBTECH 13 115.

A preferred method for identifying a compound capable of modulating the activity of PGC-3 is a scintillation proximity assay (SPA). SPA involves the use of fluomicrospheres coated with acceptor molecules, such as receptors, to which a ligand will bind selectively in a reversible manner (N Bosworth & P Towers, Nature, 341, 167–168, 1989). The technique requires the use of a ligand labelled with an isotope that emits low energy radiation which is dissipated easily into an aqueous medium. At any point during an assay, bound labelled ligands will be in close proximity to the fluomicrospheres, allowing the emitted energy to activate the fluor and produce light. In contrast, the vast majority of unbound labelled ligands will be too far from the fluomicrospheres to enable the transfer of energy. Bound ligands produce light but free ligands do not, allowing the extent of ligand binding to be measured without the need to separate bound and free ligand.

Cellular assay systems may be used to further identify PGC-3 modulators for use in the regulation of metabolism.

Therefore in a further aspect of the invention the candidate compound modulator is contacted with a host-cell which expresses an PGC-3 polypeptide (as hereindefined).

A preferred cellular assay system for use in the method of the invention is a two-hybrid assay system. The two-hybrid system utilises the ability of a pair of interacting proteins to bring the activation domain of a transcription factor into close proximity with its DNA-binding domain, restoring the functional activity of the transcription factor and inducing the expression of a reporter gene (S Fields & 0 Song, Nature, 340, 245–246, 1989). Commercially available systems such as the Clontech Matchmaker™ systems and protocols may be used with the present invention.

Other preferred cellular assay systems include measurement of changes in the levels of intracellular signalling molecules such as cyclic-AMP, intracellular calcium ions, or arachidonic acid metabolite release. These may all be measured using standard published procedures and commercially available reagents. In addition the polynucleotides of the present invention may be transfected into appropriate cell lines that have been transfected with a "reporter" gene such as bacterial lacZ, luciferase, aequorin or green fluorescent protein that will "report" these intracellular changes (Egerton et al, J. Mol, Endocrinol, 1995, 14(2), 179–189).

In a further aspect of the present invention we provide a novel PGC-3 modulator, or a pharmaceutically acceptable salt thereof, for use in a method of treatment of metabolic diseases of the human or animal body by therapy.

Examples of metabolic diseases which may be treated using a compound of the invention include insulin resistance syndrome, non-insulin dependent diabetes mellitus, dyslipidemia, obesity and atherosclerosis.

According to a further aspect of the invention, we provide a pharmaceutical composition which comprises a novel PGC-3 modulator, or a pharmaceutically acceptable salt thereof, in association with a pharmaceutically acceptable diluent or carrier.

The composition may be in the form suitable for oral use, for example a tablet, capsule, aqueous or oily solution, suspension or emulsion; for topical use, for example a cream, ointment, gel or an aqueous or oily solution or suspension; for nasal use, for example a snuff, nasal spray or nasal drops; for rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general, the above compositions may be prepared in a conventional manner using conventional excipients.

The invention also provides a method of treating a metabolic disease or medical condition mediated alone or in part by PGC-3, which comprises administering to a warm-blooded animal requiring such treatment an effective amount of an PGC-3 modulator as defined above.

The invention also provides the use of an PGC-3 modulator in the production of a medicament for use in the treatment of a metabolic disease.

The amount of active ingredient that is combined with one or more excipients to produce a single dosage form will necessarily vary depending on the subject treated and the particular route of administration. For example, a formulation intended for oral administration to humans will generally contain for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

The size of the dose for therapeutic or prophylactic purposes of an PGC-3 modulator will naturally vary according to the nature and severity of the immune disease, the age and sex of the patient, and the route of administration, according to well known principles of medicine.

In using an PGC-3 modulator for therapeutic or prophylactic purposes it will generally be administered so that a daily dose in the range for example 0.5 mg to 75 mg per kg body weight is received, given if required in divided doses. In general lower doses will be administered when a parenteral route is employed. Thus for example, for intravenous administration, a dose in the range for example 0.5 mg to 30 mg per kg body weight will generally be used. Similarly, for administration by inhalation a dose in the range for example 0.5 mg to 25 mg per kg body weight will be used.

The invention will now be illustrated but not limited by reference to the following Tables, Examples and Figures. Unless indicated otherwise, the techniques used are those detailed in well known molecular biology textbooks such as Sambrook, Fritsch & Maniatis, Molecular Cloning a Laboratory Manual, second edition, 1989, Cold Spring arbor Laboratory Press.

SEQ ID NO:1. shows the full length human PGC-3a cDNA

SEQ ID NO:2. shows human PGC-3a protein sequence

SEQ ID NO:3. shows human PGC-3b cDNA

SEQ ID NO:4. shows human PGC-3b protein sequence

SEQ ID NO:5. shows the sequence of the 3' RACE product isolated from human adipocyte cDNA.

SEQ ID NO:6. shows the sequence of the 5'RACE product isolated from human heart cDNA.

SEQ ID NO:7. shows human PGC-3c cDNA

SEQ ID NO 8. shows human PGC-3c protein sequence

SEQ ID NO 9. shows the full length rat PGC-3 cDNA

SEQ ID NO 10. shows rat PGC-3 protein sequence

FIGURE LEGENDS

FIG. 1 shows specific PCR products of 561 bp for PGC-3b and 491 bp for PGC-3a, isolated from breast adipose tissue cDNA, in lanes 1 and 2 respectively. The PGC-3b specific PCR product was obtained using PCR primers CME9830 and CME9831 (Table 2). The PGC-3a specific PCR product was obtained using PCR primers CME9830 and CME9850 (Table 2).

FIG. 3 shows a comparison of human PGC-3a (SEQ ID NO: 2) and rat PGC-3 (SEQ ID NO: 10) protein sequences indicating that the molecules share a high degree of sequence homology.

Figure 4:
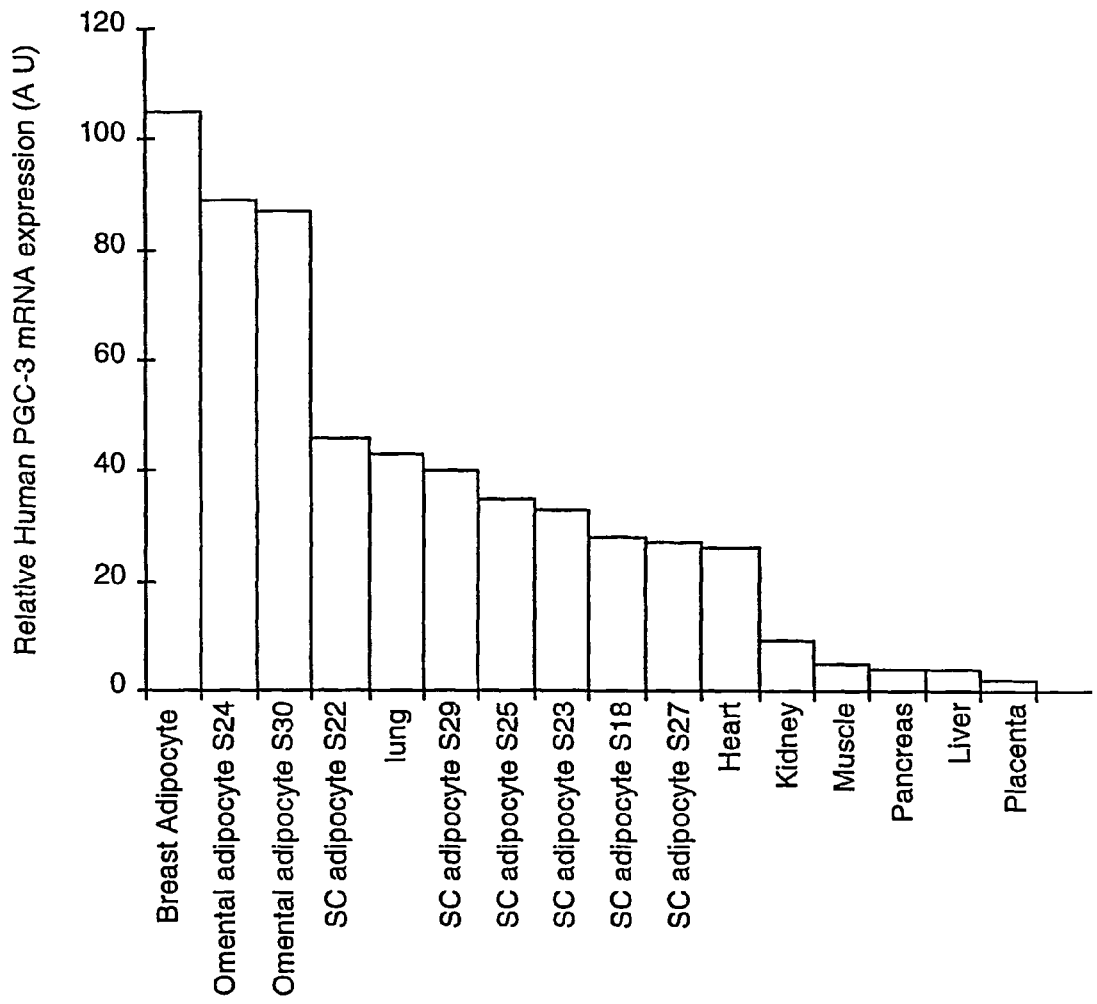

FIG. 4 shows the mean relative expression of PGC-3 mRNA in a range of human tissues. Quantitative real-time PCR was undertaken in quadruplicate on cDNA samples derived from the human tissues listed using Taqman™ fluorescent PCR technology (PE. Applied Biosystems). The normalised ratio of expression of PGC-3 relative to a housekeeping gene (GAPDH) was calculated for all tissues. SC=subcutaneous. Where multiple samples of the same tissue type were assayed the sample number is given, eg Omental adipocyte S24 refers to the data obtained from the omental adipocyte sample number 24. AU=arbitrary units.

TABLES

TABLE 1

Examples of conservative amino acid substitutions

| Original residue | Example conservative substitutions |
| --- | --- |
| Ala (A) | Gly; Ser; Val; Leu; Ile; Pro |
| Arg (R) | Lys; His; Gln; Asn |
| Asn (N) | Gln; His; Lys; Arg |
| Asp (D) | Glu |
| Cys (C) | Ser |
| Gln (Q) | Asn |
| Glu (E) | Asp |
| Gly (G) | Ala; Pro |
| His (H) | Asn; Gln; Arg; Lys |
| Ile (I) | Leu; Val; Met; Ala; Phe |
| Leu (L) | Ile; Val; Met; Ala; Phe |
| Lys (K) | Arg; Gln; His; Asn |
| Met (M) | Leu; Tyr; Ile; Phe |
| Phe (F) | Met; Leu; Tyr; Val; Ile; Ala |
| Pro (P) | Ala; Gly |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala |

TABLE 2

Primer sequences

| Primer | Sequence |
| --- | --- |
| forward primer CME 9748 | 5' GTCACAAAGCGACCCAACTT 3' (SEQ ID NO: 11) |
| reverse primer CME 9749 | 5' GAGTCATGGTCTCCAAAGGAAC 3' (SEQ ID NO: 12) |
| AP1 adaptor primer | 5' CCATCCTAATACGACTCACTATAGGGC 3' (SEQ ID NO: 13) |
| CME 9830 forward primer | 5' GCCACTCGAAGGAACTTCAGAT 3' (SEQ ID NO: 14) |
| CME 9850 reverse primer B | 5' GGGTTAAGGCTGTTATCAATGC 3' (SEQ ID NO: 15) |
| CME 9831 reverse primer A | 5' AGGCCAGAAGAGAAACAGGATG 3' (SEQ ID NO: 16) |
| CME 9726 sequencing primer | 5' CTTCTCCTGTTCCTTTGGAGAC 3' (SEQ ID NO: 17) |
| CME 9727 sequencing primer | 5' TGGGGTTCACTTGAGGATTG 3' (SEQ ID NO: 18) |
| CME 9778 sequencing primer | 5' ATTCAAAATCTCTTCCAGCGAC 3' (SEQ ID NO: 19) |
| CME 9776 sequencing primer | 5' GAAGACAGAAGCTGTGATGCTG 3' (SEQ ID NO: 20) |

TABLE 3

Primers used in Example 4

| Primer | Sequence |
|---|---|
| SP1A | 5'-CATCACAGAGCACGTCTTGAG-3' (SEQ ID NO: 21) |
| SP2A | 5'-CATGTAGCGTATGAGTTGCACCATC-3' (SEQ ID NO: 22) |
| Oligo d(T)-anchor primer | 5'-GACCACGCGTATCGATGTCGACTTTTT TTTTTTTTTTV-3' V = A, C or G (SEQ ID NO: 23) |
| PCR anchor primer | 5'-GACCACGCGTATCGATGTCGAC-3 (SEQ ID NO: 24) |

TABLE 4

Details of primers used to sequence rat PGC-3

| Primer | primer sequence (5'→3') |
|---|---|
| CVGI169 | TTGGGTAACGCCAGGGTTTTCCCAGTCAC (SEQ ID NO: 25) |
| CVGI170 | CCCCAGGCTTTACACTTTATGCTTCCGGC (SEQ ID NO: 26) |
| CVGI171 | GCCAGTACAGCCCTGATGAT (SEQ ID NO: 27) |
| CVGI172 | TCCCCAGTGTCTGAAGTGGATG (SEQ ID NO: 28) |
| CVGI281 | CTCATTCGCTACATGCATACCT (SEQ ID NO: 29) |
| CVGI282 | CGGCCTTGTGTCAAGGTGGATG (SEQ ID NO: 30) |
| CVGI283 | CTTCTGGACTGAGTTCTCCATC (SEQ ID NO: 31) |
| CVGI390 | CAGGAGACTGAATCCAGAGCTG (SEQ ID NO: 32) |
| CVGI391 | GACAGTAGTCAAGGCCAGCAGC (SEQ ID NO: 33) |
| CVGI457 | GAGACCATGACTACTGCCAGGT (SEQ ID NO: 34) |
| CVGI458 | ACCGCTCTGGAGGAGGAAGACT (SEQ ID NO: 35) |
| CVGI535 | TTAAGCCTTAACCCTTTGAGGA (SEQ ID NO: 36) |
| CVGI536 | GGCCCAGATACACCGACTATGA (SEQ ID NO: 37) |

EXAMPLES

Example 1

Isolation of Partial PGC-3 cDNA

Method:

PCR primers CME 9748 and CME 9749, listed in Table 2 were synthesised and used to amplify a 347 bp product from human adipose cDNA (Human adipocyte Marathon Ready cDNA, Clontech Cat.#7447-1, Clontech, Basingstoke, UK).

A technique known as Rapid Amplification of cDNA Ends (RACE) was then used to amplify the 3' end of the PGC-3 cDNA. RACE is a commonly used molecular biological technique which enables the user to extend and identify sequence along a cDNA template in one direction. This allows the user to obtain a complete cDNA sequence starting from a small piece of cDNA sequence. For a more complete description of the method refer to Chenchick A, Moqadam F and Siebert P. 1996 Laboratory guide to RNA: isolation, analysis and synthesis. Wiley-Liss Inc. p 273–321. In this case we used a commercially available RACE PCR kit, the Human adipocyte Marathon Ready™ cDNA (Clontech, Basingstoke, UK). It is a premade human adipocyte "library" of adaptor-ligated double stranded cDNA ready for performing both 5' and 3' RACE from the same template. The PGC-3 gene specific primer CME 9748 (Table 2) was used in a Marathon RACE reaction with the AP1 adapter primer (Table 2) supplied by Clontech and the Marathon Ready™ cDNA according to the manufacturer's instructions.

Results:

A 1.5 kb PCR product was amplified in the reaction and separated from non-specific DNA by agarose gel electrophoresis using a 1.5% agarose gel and visualised by ethidium bromide staining. The 1.5 kb PCR product was isolated from the gel using a DNA extraction kit (Qiaex II™, Qiagen) and the purified PCR product cloned into PCR2.1™ vector using a TOPO TA™ Cloning kit (Invitrogen), according to the manufacturer's instructions. The cloned PCR product was fully sequenced using the vector M13 sequencing primers supplied in the kit (Invitrogen) and the PGC-3 gene specific sequencing primers CME 9726, CME 9727, CME 9778 and CME 9776 (listed in Table 2). The sequence of the 3'RACE product is shown in FIG. 5 (SEQ ID NO: 5). The predicted protein sequence of the 3' end of SEQ ID NO:7 was found to be 50% identical to the sequence for human PGC-1 over a 135 aa region (see FIG. 7). This small region of SEQ ID NO:7 also shared 53% identity to the rat PGC-1 sequence (EMBL accession number: AB025784).

Two variants of PGC-3 have been found with cDNA sequence which differ at the 3' end. We have named these two variants PGC-3a and PGC-3b.

Example 2

Isolation of a Full Length PGC-3a Clone from a Human Heart cDNA Library.

Method:

Primers CME 9830 and CME 9850 (Table 2) were synthesised based on the PGC-3a 3' RACE product sequence. These were used to PCR screen the Origene human heart cDNA library master plate (ORIGENE LHT-1001, Origene, USA) according to the manufacturers instructions.

Results:

PCR screening of the master plate identified several wells positive for PGC-3a cDNA. The subplates corresponding to these wells were obtained from Origene and a subsequent round of PCR screening was performed to identify individual clones containing PGC-3a cDNA.

Clones containing PGC-3a were identified and sequenced. This resulted in the isolation of the complete cDNA sequence for PGC-3a (SEQ ID NO:1). The PGC-3a cDNA sequence comprises a coding region of 3009 nucleotides, that encode a protein of 1002 amino acids with a calculated molecular mass of 110 kDa and an estimated isoelectric point of 4.933. The protein sequence for PGC-3a is shown in SEQ ID NO:2.

Example 3

PCR Amplification of PGC-3a and PGC-3b from Human Breast Adipocyte cDNA

Methods:

PCR primers were synthesised which would specifically amplify either PGC-3a or PGC-3b (CME 9830, CME 9831, CME 9850, Table 2).

To investigate whether both PGC-3a and PGC-3b were expressed by human breast adipocytes, PCRs were carried out using the above primers to amplify PGC-3a and PGC-3b from human breast adipocyte cDNA. The PCR conditions used were 94° C. for 1 minute then 30 cycles of 94° C. for 30 sec, then 68° C. for 4 minutes. The DNA polymerase used was Extensor™ from Advanced Biotechnologies. PCR was performed according to standard procedure described in Molecular Cloning, a laboratory manual, Sambrook, Fritsch and Maniatis Second Ed 1989). The forward PCR primer (CME 9830) was used in combination with either reverse PCR primer A (CME 9831) designed specifically to amplify PGC-3b (sequence 2) or reverse primer B (CME 9850) designed specifically to amplify sequence 3 PGC-3a (3' RACE product).

Figure 1:
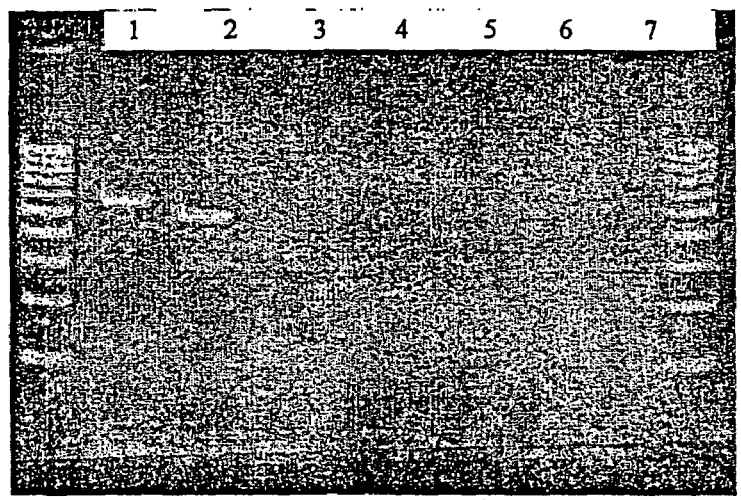
Figure 2:
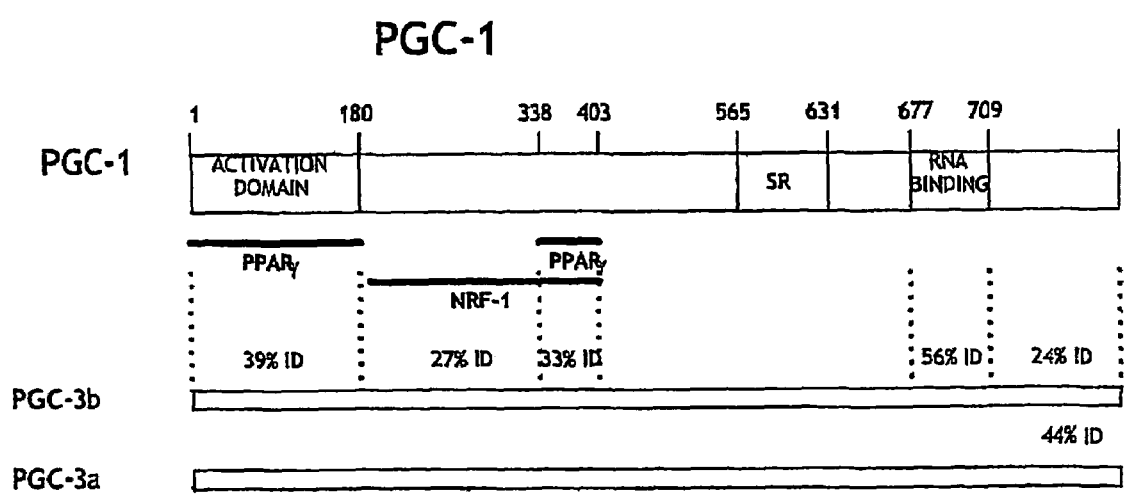
FIG. 2 shows a comparison of PGC-3a and PGC-3b with PGC-1, indicating that the molecules share regions of sequence homology in particular locations which are believed to be important for biological activity.

Results:

Specific PCR products of 561 bp for PGC-3b (CME9830/CME 9831) and 491 bp for PGC-3a (CME9830/CME9850) were obtained, as shown in FIG. 1 in lanes 1 and 2 respectively.

The complete cDNA sequence for PGC-3b is shown in SEQ ID NO:3. The PGC-3b cDNA sequence comprises a coding region of 2991 nucleotides encoding a protein of 996 amino acids. The protein sequence for PGC-3b is shown in SEQ ID NO:4.

Example 4

Isolation of Partial PGC-3c cDNA

The technique known as RACE as described in example 1 was used to amplify the 5' end of the PGC-3c cDNA. This procedure was undertaken using the Roche 5'/3'RACE kit (Cat. No. 1 734 792) and followed the manufacturer's instructions. First strand cDNA was synthesized from total human heart RNA (Stratagene, Cat. No. 735012-41) using a gene specific primer (SP1A, listed in Table 3), AMV reverse transcriptase (supplied in kit) and deoxynucleotide mix (supplied in kit). The first strand cDNA was purified using High Pure PCR Product Purification Kit (Roche Diagnostics Corporation, Indianapolis, Ind., USA—Cat No. 1 732 668) according to the manufacturer's instructions. A homopolymeric A-tail was then added to the 3'end of the cDNA using terminale transferase using reagents and instructions supplied with the kit. The cDNA was then amplified by PCR using a gene specific primer (SP2A, see table 3) and an oligo dT-anchor primer (see table 3). The obtained cDNA was further amplified by a second PCR using a nested specific primer (SP3A, see Table 3) and a PCR anchor primer (see table 3). Resulting 5'RACE products were cloned into a vector. The cloned PCR products were fully sequenced. The sequence of the 5'RACE product is shown in Figure SEQ ID NO: 6. The full length cDNA sequence of PGC-3c is shown in SEQ ID NO: 7. The predicted protein sequence of PGC-3c is shown in SEQ ID NO: 8.

Example 5

Isolation of Full Length Rat PGC-3 cDNA

Homology searching using the human PGC-3 cDNA sequence identified a rat clone in a proprietary database that had a high level of homology to PGC-3. This clone was obtained and sequenced using primers CVGI169, CVGI170, CVGI171, CVGI172, CVGI281, CVGI282, CVGI283, CVGI390, CVGI391, CVGI457, CVGI458, CVGI535 (see table 4 for sequence information). The full length rat PGC-3 cDNA sequence is shown in SEQ ID NO: 9. The predicted protein sequence of rat PGC-3 is shown in Figure SEQ ID NO: 10. FIG. 13 shows a comparison of human PGC-3a and rat PGC-3 protein sequences, indicating that the molecules have a high degree of sequence homology (greater than 78% identity).

Example 6

Comparison of Human PGC-3 mRNA Expression Between Tissues

Total RNA was extracted from human adipocytes using TR1 reagent (Sigma-Aldrich) following the manufacturer's suggested protocol. Two micrograms of total RNA from each adipocyte samples was used to generate cDNA, using the Promega reverse transcription system (Promega; catalogue number A3500) according to the manufacturer's instructions. The heart, skeletal muscle, kidney, liver, lung, heart and pancreas cDNAs were obtained from Clontech (Clontech, catalogue numbers K1420-1 and K1421-1). Probe and primer sequences were designed for PGC-3 and were: PGC-3 forward primer; 5'-TGCTGGCCCAGATA-CACTGA-3' (SEQ ID NO: 38). PGC-3 reverse primer; 5'-GGCTGTTATCAATGCAGGCTC-3' (SEQ ID NO: 39). PGC-3 probe; 5-FAM-CGTCAGGGAAAAGCAAGTAT-GAAGCCAT-TAMRA-3' (SEQ ID NO: 40). Taqman PCR assays for each target gene were performed in quadruplicate in 96 well plates on an ABI

The invention claimed is:

1. An isolated and purified polynucleotide comprising a nucleic acid sequence which encodes a polypeptide having at least about 90% homology to a member selected from any one of:
   (a) SEQ ID NO: 2, SEQ ID NO: 2 positions 1–600, SEQ ID NO: 2 positions 400–1002, and SEQ ID NO: 2 positions 200–800, or
   (b) SEQ ID NO: 4, SEQ ID NO: 4 positions 1–600, SEQ ID NO: 4 positions 400–996, and SEQ ID NO: 4 positions 200–800, or
   (c) SEQ ID NO: 8, SEQ ID NO: 8 positions 1–600, SEQ ID NO: 8 positions 400–1023, and SEQ ID NO: 8 positions 200–800,
   wherein said polypeptide regulates the transcriptional activity of PPAR-γ.

2. A polynucleotide which comprises the human PGC-3a cDNA sequence set out in SEQ ID NO: 1.

3. A polynucleotide which comprises the human PGC-3b cDNA sequence set out in SEQ ID NO: 3.

4. A polynucleotide which comprises the human PGC-3c cDNA sequence set out in SEQ ID NO: 7.

5. An expression vector comprising a polynucleotide according to any of claims 1–4.

6. A transformed host cell comprising a polynucleotide according to any of claims 1–4.

7. An isolated and purified polynucleotide molecule comprising a nucleic acid sequence which encodes a polypeptide having at least about 90% homology to any one of SEQ ID NO: 10 positions 1–600, SEQ ID NO: 10 positions 400–990, and SEQ ID NO: 10 positions 200–800, wherein said polypeptide regulates the transcriptional activity of PPAR-γ.

8. A purified polypeptide comprising the human PGC-3a amino acid sequence set out in SEQ D NO: 2; or a variant of SEQ ID NO: 2 having at least about 90% homology to a member selected from: SEQ ID NO: 2 positions 1–600, SEQ ID NO: 2 positions 400–1002, or SEQ ID NO: 2 positions 200–800, wherein said variant regulates the transcriptional activity of PPAR-γ, or a biologically active fragment thereof, wherein the fragment regulates the transcriptional activity of PPAR-γ.

9. A purified polypeptide comprising the human PGC-3b amino acid sequence set out in SEQ D NO: 4; or a variant of SEQ ID NO: 4 having at least about 90% homology to a member selected from: SEQ ID NO: 4 positions 1–600, SEQ ID NO: 4 positions 400–996, or SEQ ID NO: 4 positions 200–800, wherein said variant regulates the transcriptional activity of PPAR-γ, or a biologically active fragment thereof, wherein the fragment regulates the transcriptional activity of PPAR-γ.

10. A purified polypeptide comprising the human PGC-3c amino acid sequence set out in SEQ ID NO: 8; or a variant of SEQ ID NO: 8 having at least about 90% homology to a member selected from: SEQ ID NO: 8 positions 1–600, SEQ ID NO: 8 positions 400–1023, or SEQ ID NO: 8 positions 200–800, wherein said variant regulates the transcriptional activity of PPAR-γ, or a biologically active fragment thereof, wherein the fragment regulates the transcriptional activity of PPAR-γ.

11. A purified polypeptide comprising the rat PGC-3 amino acid sequence set out in SEQ ID NO: 10; or a variant of SEQ ID NO: 10 having at least about 90% homology to a member selected from: SEQ ID NO; 10 positions 1–600, SEQ ID NO: 10 positions 400–990, or SEQ ID NO: 10 positions 200–800, wherein said variant regulates the transcriptional activity of PPAR-γ, or a biologically active fragment thereof, wherein the fragment regulates the transcriptional activity of PPAR-γ.

12. A method for identifying a therapeutic agent capable of modulating the activity of PGC-3 for use in the regulation of metabolism, which method comprises:
   (i) contacting a candidate compound modulator with a PGC-3 polypeptide comprising any one of
      (a) the amino acid sequence set out in SEQ ID NO: 2; or a variant of SEQ ID NO: 2 having at least about 90% homology to a member selected from; SEQ ID NO: 2 positions 1–600, SEQ ID NO: 2 positions 400–1002, or SEQ ID NO: 2 positions 200–800, wherein said variant regulates the transcriptional activity of PPAR-γ, or a biologically active fragment thereof, wherein the fragment regulates the transcriptional activity of PPAR-γ, or (b) the amino acid sequence set out in SEQ ID NO: 4; or a variant of SEQ ID NO: 4 having at least about 90% homology to a member selected from: SEQ ID NO: 4 positions 1–600, SEQ ID NO: 4 positions 400–996, or SEQ ID NO: 4 positions 200–800, wherein said variant regulates the transcriptional activity of PPAR-γ, or a biologically active fragment thereof, wherein the fragment regulates the transcriptional activity of PPAR-γ, or (c) the amino acid sequence set out in SEQ ID NO: 8; or a variant of SEQ ID NO: 8 having at least about 90% homology to a member selected from: SEQ ID NO: 8 positions 1–600, SEQ ID NO: 8 positions 400–996, or SEQ ID NO: 8 positions 200–800, wherein said variant regulates the transcriptional activity of PPAR-γ; or a biologically active fragment thereof, wherein the fragment regulates the transcriptional activity of PPAR-γ, and (ii) measuring an effect of the candidate compound modulator on the activity of the PGC-3 polypeptide.

13. A method as claimed in claim 12, wherein the candidate compound modulator is contacted with a host-cell which expresses a PGC-3 polypeptide.

* * * * *

SEQUENCE LISTING

<160> NUMBER OF SEQ ID NOS: 40

<210> SEQ ID NO 1
<211> LENGTH: 3203
<212> TYPE: DNA
<213> ORGANISM: Homo sapiens

<400> SEQUENCE: 1
ggcacgagga agaattgaac tcatacagct gatgggagtg tacaaaggtg gagggtccgg     60
ggaggagcaa ctctatgctg actttccaga acttgacctc tcccagctgg atgccagcga    120
ctttgactcg gccacctgct ttggggagct gcagtggtgc ccagagaact cagagactga    180

-continued

```
acccaaccag tacagccccg atgactccga gctcttccag attgacagtg agaatgaggc    240
cctcctggca gagctcacca agaccctgga tgacatccct gaagatgacg tgggtctggc    300
tgccttccca gccctggatg gtggagacgc tctatcatgc acctcagctt cgcctgcccc    360
ctcatctgca ccccccagcc ctgccccgga gaagccctcg gccccagccc ctgaggtgga    420
cgagctctca ctgctgcaga agctcctcct ggccacatcc tacccaacat caagctctga    480
cacccagaag gaagggaccg cctggcgcca ggcaggcctc agatctaaaa gtcaacggcc    540
ttgtgttaag gcggacagca cccaagacaa gaaggctccc atgatgcagt ctcagagccg    600
aagttgtaca gaactacata gcacctcac ctcggcacag tgctgcctgc aggatcgggg    660
tctgcagcca ccatgcctcc agagtccccg gctccctgcc aaggaggaca aggagccggg    720
tgaggactgc ccgagccccc agccagctcc agcctctccc caggactccc tagctctggg    780
cagggcagac cccggtgccc cggtttccca ggaagacatg caggcgatgg tgcaactcat    840
acgctacatg cacacctact gcctccccca gaggaagctg cccccacaga cccctgagcc    900
actccccaag gcctgcagca acccctccca gcaggtcaga tcccggccct ggtcccggca    960
ccactccaaa gcctcctggg ctgagttctc cattctgagg gaacttctgg ctcaagacgt   1020
gctctgtgat gtcagcaaac cctaccgtct ggccacgcct gtttatgcct ccctcacacc   1080
tcggtcaagg cccaggcccc ccaaagacag tcaggcctcc cctggtcgcc cgtcctcggt   1140
ggaggaggta aggatcgcag cttcacccaa gagcaccggg cccagaccaa gcctgcgccc   1200
actgcggctg gaggtgaaaa gggaggtccg ccggcctgcc agactgcagc agcaggagga   1260
ggaagacgag gaagaagagg aggaggaaga ggaagaagaa aaagaggagg aggaggagtg   1320
gggcaggaaa aggccaggcc gaggcctgcc atggacgaag ctggggagga agctggagag   1380
ctctgtgtgc cccgtgcggc gttctcggag actgaaccct gagctgggcc cctggctgac   1440
atttgcagat gagccgctgg tcccctcgga gccccaaggt gctctgccct cactgtgcct   1500
ggctcccaag gcctacgacg tagagcggga gctgggcagc cccacggacg aggacagtgg   1560
ccaagaccag cagctcctac ggggacccca gatccctgcc ctggagagcc cctgtgagag   1620
tgggtgtggg gacatggatg aggaccccag ctgcccgcag ctccctccca gagactctcc   1680
caggtgcctc atgctggcct tgtcacaaag cgacccaact tttggcaaga agagctttga   1740
gcagaccttg acagtggagc tctgtggcac agcaggactc accccaccca ccacaccacc   1800
gtacaagccc acagaggagg atcccttcaa accagacatc aagcatagtc taggcaaaga   1860
aatagctctc agcctcccct cccctgaggg cctctcactc aaggccaccc cagggctgc    1920
ccacaagctg ccaaagaagc acccagagcc aagtgagctc ctgtcccacc tgcgacatgc   1980
cacagcccag ccagcctccc aggctggcca gaagcgtccc ttctcctgtt cctttggaga   2040
ccatgactac tgccaggtgc tccgaccaga aggcgtcctg caaaggaagg tgctgaggtc   2100
ctgggagccg tctggggttc accttgagga ctggcccag caggtgcccc ttgggctga    2160
ggcacaggcc cctggcaggg aggaagacag aagctgtgat gctggtgccc cacccaagga   2220
cagcacgctg ctgagagacc atgagatccg tgctagcctc accaaacact ttgggctgct   2280
ggagaccgcc ctggaggagg aagacctggc ctcctgcaag agccctgagt atgacactgt   2340
cttttgaagac agcagcagca gcagcggcga gagcagcttc ctcccagagg aggaagagga   2400
agaaggggag gaggaggagg aggacgatga agaagaggac tcagggtca gccccacttg    2460
ctctgaccac tgcccctacc agagcccacc aagcaaggcc aaccggcagc tctgttcccg    2520
cagccgctca agctctggct cttcaccctg ccactcctgg tcaccagcca ctcgaaggaa   2580
```

-continued

```
cttcagatgt gagagcagag ggccgtgttc agacagaacg ccaagcatcc ggcacgccag    2640
gaagcggcgg gaaaaggcca ttggggaagg ccgcgtggtg tacattcaaa atctctccag    2700
cgacatgagc tcccgagagc tgaagaggcg ctttgaagtg tttggtgaga ttgaggagtg    2760
cgaggtgctg acaagaaata ggagaggcga gaagtacggc ttcatcacct accggtgttc    2820
tgagcacgcg gccctctctt tgacaaaggg cgctgccctg aggaagcgca acgagccctc    2880
cttccagctg agctacggag ggctccggca cttctgctgg cccagataca ctgactacga    2940
ttccaattca gaagaggccc ttcctgcgtc agggaaaagc aagtatgaag ccatggattt    3000
tgacagctta ctgaaagagg cccagcagag cctgcattga taacagcctt aaccctcgag    3060
gaatacctca atacctcaga caaggccctt ccaatatgtt tacgttttca agaaatcaa     3120 gtatatgagg agagcgagcg agcgtgagag aacacccgtg agagagactt gaaactgctg    3180
tcctttaaaa aaaaaaaaa aaa                                              3203
```

<210> SEQ ID NO 2
<211> LENGTH: 1002
<212> TYPE: PRT
<213> ORGANISM: Homo sapiens

<400> SEQUENCE: 2

```
Met Gly Val Tyr Lys Gly Gly Ser Gly Glu Glu Gln Leu Tyr Ala
1               5                   10                  15

Asp Phe Pro Glu Leu Asp Leu Ser Gln Leu Asp Ala Ser Asp Phe Asp
                20                  25                  30

Ser Ala Thr Cys Phe Gly Glu Leu Gln Trp Cys Pro Glu Asn Ser Glu
            35                  40                  45

Thr Glu Pro Asn Gln Tyr Ser Pro Asp Asp Ser Glu Leu Phe Gln Ile
        50                  55                  60

Asp Ser Glu Asn Glu Ala Leu Leu Ala Glu Leu Thr Lys Thr Leu Asp
65                  70                  75                  80

Asp Ile Pro Glu Asp Asp Val Gly Leu Ala Ala Phe Pro Ala Leu Asp
                85                  90                  95

Gly Gly Asp Ala Leu Ser Cys Thr Ser Ala Ser Pro Ala Pro Ser Ser
                100                 105                 110

Ala Pro Ser Pro Ala Pro Glu Lys Pro Ser Ala Pro Ala Pro Glu
            115                 120                 125

Val Asp Glu Leu Ser Leu Leu Gln Lys Leu Leu Leu Ala Thr Ser Tyr
130                 135                 140

Pro Thr Ser Ser Ser Asp Thr Gln Lys Glu Gly Thr Ala Trp Arg Gln
145                 150                 155                 160

Ala Gly Leu Arg Ser Lys Ser Gln Arg Pro Cys Val Lys Ala Asp Ser
                165                 170                 175

Thr Gln Asp Lys Lys Ala Pro Met Met Gln Ser Gln Ser Arg Ser Cys
            180                 185                 190

Thr Glu Leu His Lys His Leu Thr Ser Ala Gln Cys Cys Leu Gln Asp
        195                 200                 205

Arg Gly Leu Gln Pro Pro Cys Leu Gln Ser Pro Arg Leu Pro Ala Lys
    210                 215                 220

Glu Asp Lys Glu Pro Gly Glu Asp Cys Pro Ser Gln Pro Ala Pro
225                 230                 235                 240

Ala Ser Pro Gln Asp Ser Leu Ala Leu Gly Arg Ala Asp Pro Gly Ala
                245                 250                 255
```

-continued

```
Pro Val Ser Gln Glu Asp Met Gln Ala Met Val Gln Leu Ile Arg Tyr
            260                 265                 270
Met His Thr Tyr Cys Leu Pro Gln Arg Lys Leu Pro Pro Gln Thr Pro
        275                 280                 285
Glu Pro Leu Pro Lys Ala Cys Ser Asn Pro Ser Gln Gln Val Arg Ser
    290                 295                 300
Arg Pro Trp Ser Arg His His Ser Lys Ala Ser Trp Ala Glu Phe Ser
305                 310                 315                 320
Ile Leu Arg Glu Leu Leu Ala Gln Asp Val Leu Cys Asp Val Ser Lys
                325                 330                 335
Pro Tyr Arg Leu Ala Thr Pro Val Tyr Ala Ser Leu Thr Pro Arg Ser
            340                 345                 350
Arg Pro Arg Pro Pro Lys Asp Ser Gln Ala Ser Pro Gly Arg Pro Ser
        355                 360                 365
Ser Val Glu Glu Val Arg Ile Ala Ala Ser Pro Lys Ser Thr Gly Pro
    370                 375                 380
Arg Pro Ser Leu Arg Pro Leu Arg Leu Glu Val Lys Arg Glu Val Arg
385                 390                 395                 400
Arg Pro Ala Arg Leu Gln Gln Gln Glu Glu Asp Glu Glu Glu Glu Glu
                405                 410                 415
Glu Glu Glu Glu Glu Glu Glu Lys Glu Glu Glu Glu Trp Gly Arg
            420                 425                 430
Lys Arg Pro Gly Arg Gly Leu Pro Trp Thr Lys Leu Gly Arg Lys Leu
        435                 440                 445
Glu Ser Ser Val Cys Pro Val Arg Arg Ser Arg Leu Asn Pro Glu
    450                 455                 460
Leu Gly Pro Trp Leu Thr Phe Ala Asp Glu Pro Leu Val Pro Ser Glu
465                 470                 475                 480
Pro Gln Gly Ala Leu Pro Ser Leu Cys Leu Ala Pro Lys Ala Tyr Asp
                485                 490                 495
Val Glu Arg Glu Leu Gly Ser Pro Thr Asp Glu Asp Ser Gly Gln Asp
            500                 505                 510
Gln Gln Leu Leu Arg Gly Pro Gln Ile Pro Ala Leu Glu Ser Pro Cys
        515                 520                 525
Glu Ser Gly Cys Gly Asp Met Asp Glu Asp Pro Ser Cys Pro Gln Leu
    530                 535                 540
Pro Pro Arg Asp Ser Pro Arg Cys Leu Met Leu Ala Leu Ser Gln Ser
545                 550                 555                 560
Asp Pro Thr Phe Gly Lys Lys Ser Phe Glu Gln Thr Leu Thr Val Glu
                565                 570                 575
Leu Cys Gly Thr Ala Gly Leu Thr Pro Thr Thr Pro Pro Tyr Lys
            580                 585                 590
Pro Thr Glu Glu Asp Pro Phe Lys Pro Asp Ile Lys His Ser Leu Gly
        595                 600                 605
Lys Glu Ile Ala Leu Ser Leu Pro Ser Pro Glu Gly Leu Ser Leu Lys
    610                 615                 620
Ala Thr Pro Gly Ala Ala His Lys Leu Pro Lys Lys His Pro Glu Arg
625                 630                 635                 640
Ser Glu Leu Leu Ser His Leu Arg His Ala Thr Ala Gln Pro Ala Ser
                645                 650                 655
Gln Ala Gly Gln Lys Arg Pro Phe Ser Cys Ser Phe Gly Asp His Asp
            660                 665                 670
Tyr Cys Gln Val Leu Arg Pro Glu Gly Val Leu Gln Arg Lys Val Leu
```

```
                       675                 680                 685
        Arg Ser Trp Glu Pro Ser Gly Val His Leu Glu Asp Trp Pro Gln Gln
            690                 695                 700
        Gly Ala Pro Trp Ala Glu Ala Gln Ala Pro Gly Arg Glu Glu Asp Arg
        705                 710                 715                 720
        Ser Cys Asp Ala Gly Ala Pro Pro Lys Asp Ser Thr Leu Leu Arg Asp
                        725                 730                 735
        His Glu Ile Arg Ala Ser Leu Thr Lys His Phe Gly Leu Leu Glu Thr
                    740                 745                 750
        Ala Leu Glu Glu Glu Asp Leu Ala Ser Cys Lys Ser Pro Glu Tyr Asp
                755                 760                 765
        Thr Val Phe Glu Asp Ser Ser Ser Ser Gly Glu Ser Ser Phe Leu
        770                 775                 780
        Pro Glu Glu Glu Glu Glu Gly Glu Glu Glu Glu Asp Asp Glu
        785                 790                 795                 800
        Glu Glu Asp Ser Gly Val Ser Pro Thr Cys Ser Asp His Cys Pro Tyr
                        805                 810                 815
        Gln Ser Pro Pro Ser Lys Ala Asn Arg Gln Leu Cys Ser Arg Ser Arg
                    820                 825                 830
        Ser Ser Ser Gly Ser Ser Pro Cys His Ser Trp Ser Pro Ala Thr Arg
                835                 840                 845
        Arg Asn Phe Arg Cys Glu Ser Arg Gly Pro Cys Ser Asp Arg Thr Pro
        850                 855                 860
        Ser Ile Arg His Ala Arg Lys Arg Glu Lys Ala Ile Gly Glu Gly
        865                 870                 875                 880
        Arg Val Val Tyr Ile Gln Asn Leu Ser Ser Asp Met Ser Ser Arg Glu
                        885                 890                 895
        Leu Lys Arg Arg Phe Glu Val Phe Gly Glu Ile Glu Glu Cys Glu Val
                    900                 905                 910
        Leu Thr Arg Asn Arg Arg Gly Glu Lys Tyr Gly Phe Ile Thr Tyr Arg
                915                 920                 925
        Cys Ser Glu His Ala Ala Leu Ser Leu Thr Lys Gly Ala Ala Leu Arg
        930                 935                 940
        Lys Arg Asn Glu Pro Ser Phe Gln Leu Ser Tyr Gly Gly Leu Arg His
        945                 950                 955                 960
        Phe Cys Trp Pro Arg Tyr Thr Asp Tyr Asp Ser Asn Ser Glu Glu Ala
                        965                 970                 975
        Leu Pro Ala Ser Gly Lys Ser Lys Tyr Glu Ala Met Asp Phe Asp Ser
                    980                 985                 990
        Leu Leu Lys Glu Ala Gln Gln Ser  Leu His
                995                 1000

<210> SEQ ID NO 3
<211> LENGTH: 3679
<212> TYPE: DNA
<213> ORGANISM: Homo sapiens

<400> SEQUENCE: 3
ggcacgagga agaattgaac tcatacagct gatgggagtg tacaaaggtg gagggtccgg      60
ggaggagcaa ctctatgctg actttccaga acttgacctc tcccagctgg atgccagcga     120
ctttgactcg gccacctgct ttggggagct gcagtggtgc ccagagaact cagagactga     180
acccaaccag tacagccccg atgactccga gctcttccag attgacagtg agaatgaggc     240
cctcctggca gagctcacca agaccctgga tgacatccct gaagatgacg tgggtctggc     300
```

-continued

```
tgccttccca gccctggatg gtggagacgc tctatcatgc acctcagctt cgcctgcccc    360
ctcatctgca ccccccagcc ctgccccgga gaagccctcg gccccagccc ctgaggtgga    420
cgagctctca ctgctgcaga agctcctcct ggccacatcc tacccaacat caagctctga    480
cacccagaag gaagggaccg cctggcgcca ggcaggcctc agatctaaaa gtcaacggcc    540
ttgtgttaag gcggacagca cccaagacaa gaaggctccc atgatgcagt ctcagagccg    600
aagttgtaca gaactacata agcacctcac ctcggcacag tgctgcctgc aggatcgggg    660
tctgcagcca ccatgcctcc agagtccccg gctccctgcc aaggaggaca ggagccgggg    720
tgaggactgc ccgagccccc agccagctcc agcctctccc caggactccc tagctctggg    780
cagggcagac cccggtgccc cggtttccca ggaagacatg caggcgatgg tgcaactcat    840
acgctacatg cacacctact gcctccccca gaggaagctg cccccacaga cccctgagcc    900 actcccaag gcctgcagca cccctccca gcaggtcaga tcccggccct ggtcccggca    960
ccactccaaa gcctcctggg ctgagttctc cattctgagg gaacttctgg ctcaagacgt   1020
gctctgtgat gtcagcaaac cctaccgtct ggccacgcct gtttatgcct ccctcacacc   1080
tcggtcaagg cccaggcccc ccaaagacag tcaggcctcc cctggtcgcc cgtcctcggt   1140 ggaggagta aggatcgcag cttcacccaa gagcaccggg cccagaccaa gcctgcgccc   1200
actgcggctg gaggtgaaaa gggaggtccg ccggcctgcc agactgcagc agcaggagga   1260
ggaagacgag gaagaagagg aggaggaaga ggaagaagaa aaagaggagg aggaggagtg   1320
gggcaggaaa aggccaggcc gaggcctgcc atggacgaag ctggggagga agctggagag   1380
ctctgtgtgc cccgtgcggc gttctcggag actgaaccct gagctgggcc cctggctgac   1440
atttgcagat gagccgctgg tcccctcgga gccccaaggt gctctgccct cactgtgcct   1500
ggctcccaag gcctacgacg tagagcggga gctgggcagc ccacggacg aggacagtgg   1560 ccaagaccag cagctcctac ggggacccca gatccctgcc ctggagagcc cctgtgagag   1620
tgggtgtggg gacatggatg aggaccccag ctgcccgcag ctccctccca gagactctcc   1680
caggtgcctc atgctggcct tgtcacaaag cgacccaact tttggcaaga gagctttga   1740 gcagaccttg acagtggagc tctgtggcac agcaggactc accccaccca ccacaccacc   1800
gtacaagccc acagaggagg atcccttcaa accagacatc aagcatagtc taggcaaaga   1860
aatagctctc agcctcccct cccctgaggg cctctcactc aaggccaccc cagggctgc    1920 ccacaagctg ccaaagaagc acccagagcg aagtgagctc ctgtcccacc tgcgacatgc   1980
cacagcccag ccagcctccc aggctggcca gaagcgtccc ttctcctgtt cctttggaga   2040
ccatgactac tgccaggtgc tccgaccaga aggcgtcctg caaaggaagg tgctgaggtc   2100
ctgggagccg tctggggttc accttgagga ctggcccag cagggtgccc cttgggctga    2160
ggcacaggcc cctggcaggg aggaagacag aagctgtgat gctggcgccc cacccaagga   2220
cagcacgctg ctgagagacc atgagatccg tgccagcctc accaaacact tgggctgct    2280 ggagaccgcc ctgaggagg aagacctggc ctcctgcaag agccctgagt atgacactgt   2340
ctttgaagac agcagcagca gcagcggcga gagcagcttc ctcccagagg aggaagagga   2400
agaaggggag gaggaggagg aggacgatga agaagaggac tcaggggtca gccccacttg   2460
ctctgaccac tgcccctacc agagcccacc aagcaaggcc aacggcagc tctgttcccg    2520 cagccgctca agctctggct cttcaccctg ccactcctgg tcaccagcca ctcgaaggaa   2580
cttcagatgt gagagcagag ggccgtgttc agacagaacg ccaagcatcc ggcacgccag   2640
```

-continued

```
gaagcggcgg gaaaaggcca ttggggaagg ccgcgtggtg tacattcaaa atctctccag   2700
cgacatgagc tcccgagagc tgaagaggcg ctttgaagtg tttggtgaga ttgaggagtg   2760
cgaggtgctg acaagaaata ggagaggcga gaagtacggc ttcatcacct accggtgttc   2820
tgagcacgcg gccctctctt tgacaaaggg cgctgccctg aggaagcgca acgagccctc   2880
cttccagctg agctacggag ggctccggca cttctgctgg cccagataca ctgactacgg   2940
taagcccctg aaacccagcc acagtctagt aagactcaaa gcttgggaag cagtgccttc   3000
cttgaacaaa acccagagct aaagcgcctt gtggacatag cttccatccc cacaccccag   3060
tgtgctgctt ggtataactt tgcagccact ttgcctgaag actaccatcc tgtttctctt   3120
ctggcctctg gtccacctta tcctgtcctg tgactgctac caaagagaat ccagcctccc   3180

acggcctcta ggaagattca gtcatgtgca cagccagctg gcagaaccgt ggctacggtc   3240
tccttgactt cacagggcca gctgctaccc tgtccccttc aggggcattc cgtggtgacc   3300
ccagacaagg cagcagccac ctggggacaa gatgatgaag aaggacaaag aagtacaatg   3360
tacgaaagaa ttacttggcc aggctcagtg gctcatgcct gtaatcccat caccttggga   3420
ggctgaggca agaggatcac ttgagcccag gagttcgaga ccagcttggg caacatagtg   3480
aaatcctgtc tctacaaaaa atataaaaat tagccaggca tggtggcttg cgcctatagt   3540
cccagctact caggaggcag aggtgggagg atcacctgaa cccaagaggt tggagctgca   3600
gtgagccatg atggcactac tgcattccag cctgggcaac agagcaagac cctgtctcaa   3660
aaggaaaaaa aaaaaaaaa                                                3679
```

```

<210> SEQ ID NO 4
<211> LENGTH: 996
<212> TYPE: PRT
<213> ORGANISM: Homo sapiens

<400> SEQUENCE: 4

Met Gly Val Tyr Lys Gly Gly Gly Ser Gly Glu Glu Gln Leu Tyr Ala
1               5                   10                  15

Asp Phe Pro Glu Leu Asp Leu Ser Gln Leu Asp Ala Ser Asp Phe Asp
            20                  25                  30

Ser Ala Thr Cys Phe Gly Glu Leu Gln Trp Cys Pro Glu Asn Ser Glu
        35                  40                  45

Thr Glu Pro Asn Gln Tyr Ser Pro Asp Asp Ser Glu Leu Phe Gln Ile
    50                  55                  60

Asp Ser Glu Asn Glu Ala Leu Leu Ala Glu Leu Thr Lys Thr Leu Asp
65                  70                  75                  80

Asp Ile Pro Glu Asp Asp Val Gly Leu Ala Ala Phe Pro Ala Leu Asp
                85                  90                  95

Gly Gly Asp Ala Leu Ser Cys Thr Ser Ala Ser Pro Ala Pro Ser Ser
            100                 105                 110

Ala Pro Pro Ser Pro Ala Pro Glu Lys Pro Ser Ala Pro Ala Pro Glu
        115                 120                 125

Val Asp Glu Leu Ser Leu Leu Gln Lys Leu Leu Leu Ala Thr Ser Tyr
    130                 135                 140

Pro Thr Ser Ser Ser Asp Thr Gln Lys Glu Gly Thr Ala Trp Arg Gln
145                 150                 155                 160

Ala Gly Leu Arg Ser Lys Ser Gln Arg Pro Cys Val Lys Ala Asp Ser
                165                 170                 175

Thr Gln Asp Lys Lys Ala Pro Met Met Gln Ser Gln Ser Arg Ser Cys
            180                 185                 190
```

```
Thr Glu Leu His Lys His Leu Thr Ser Ala Gln Cys Cys Leu Gln Asp
        195                 200                 205

Arg Gly Leu Gln Pro Pro Cys Leu Gln Ser Pro Arg Leu Pro Ala Lys
        210                 215                 220

Glu Asp Lys Glu Pro Gly Glu Asp Cys Pro Ser Pro Gln Pro Ala Pro
225                 230                 235                 240

Ala Ser Pro Gln Asp Ser Leu Ala Leu Gly Arg Ala Asp Pro Gly Ala
                245                 250                 255

Pro Val Ser Gln Glu Asp Met Gln Ala Met Val Gln Leu Ile Arg Tyr
            260                 265                 270

Met His Thr Tyr Cys Leu Pro Gln Arg Lys Leu Pro Pro Gln Thr Pro
        275                 280                 285

Glu Pro Leu Pro Lys Ala Cys Ser Asn Pro Ser Gln Gln Val Arg Ser
        290                 295                 300

Arg Pro Trp Ser Arg His His Ser Lys Ala Ser Trp Ala Glu Phe Ser
305                 310                 315                 320

Ile Leu Arg Glu Leu Leu Ala Gln Asp Val Leu Cys Asp Val Ser Lys
                325                 330                 335

Pro Tyr Arg Leu Ala Thr Pro Val Tyr Ala Ser Leu Thr Pro Arg Ser
            340                 345                 350

Arg Pro Arg Pro Lys Asp Ser Gln Ala Ser Pro Gly Arg Pro Ser
        355                 360                 365

Ser Val Glu Glu Val Arg Ile Ala Ala Ser Pro Lys Ser Thr Gly Pro
    370                 375                 380

Arg Pro Ser Leu Arg Pro Leu Arg Leu Glu Val Lys Arg Glu Val Arg
385                 390                 395                 400

Arg Pro Ala Arg Leu Gln Gln Gln Glu Glu Asp Glu Glu Glu
                405                 410                 415

Glu Glu Glu Glu Glu Glu Lys Glu Glu Glu Glu Trp Gly Arg
            420                 425                 430

Lys Arg Pro Gly Arg Gly Leu Pro Trp Thr Lys Leu Gly Arg Lys Leu
        435                 440                 445

Glu Ser Ser Val Cys Pro Val Arg Arg Ser Arg Arg Leu Asn Pro Glu
450                 455                 460

Leu Gly Pro Trp Leu Thr Phe Ala Asp Glu Pro Leu Val Pro Ser Glu
465                 470                 475                 480

Pro Gln Gly Ala Leu Pro Ser Leu Cys Leu Ala Pro Lys Ala Tyr Asp
                485                 490                 495

Val Glu Arg Glu Leu Gly Ser Pro Thr Asp Glu Asp Ser Gly Gln Asp
            500                 505                 510

Gln Gln Leu Leu Arg Gly Pro Gln Ile Pro Ala Leu Glu Ser Pro Cys
        515                 520                 525

Glu Ser Gly Cys Gly Asp Met Asp Glu Asp Pro Ser Cys Pro Gln Leu
        530                 535                 540

Pro Pro Arg Asp Ser Pro Arg Cys Leu Met Leu Ala Leu Ser Gln Ser
545                 550                 555                 560

Asp Pro Thr Phe Gly Lys Lys Ser Phe Glu Gln Thr Leu Thr Val Glu
                565                 570                 575

Leu Cys Gly Thr Ala Gly Leu Thr Pro Thr Thr Pro Pro Tyr Lys
            580                 585                 590

Pro Thr Glu Glu Asp Pro Phe Lys Pro Asp Ile Lys His Ser Leu Gly
        595                 600                 605
```

```
Lys Glu Ile Ala Leu Ser Leu Pro Ser Pro Glu Gly Leu Ser Leu Lys
        610                 615                 620

Ala Thr Pro Gly Ala Ala His Lys Leu Pro Lys Lys His Pro Glu Arg
625                 630                 635                 640

Ser Glu Leu Leu Ser His Leu Arg His Ala Thr Ala Gln Pro Ala Ser
                645                 650                 655

Gln Ala Gly Gln Lys Arg Pro Phe Ser Cys Ser Phe Gly Asp His Asp
            660                 665                 670

Tyr Cys Gln Val Leu Arg Pro Glu Gly Val Leu Gln Arg Lys Val Leu
        675                 680                 685

Arg Ser Trp Glu Pro Ser Gly Val His Leu Glu Asp Trp Pro Gln Gln
690                 695                 700

Gly Ala Pro Trp Ala Glu Ala Gln Ala Pro Gly Arg Glu Glu Asp Arg
705                 710                 715                 720

Ser Cys Asp Ala Gly Ala Pro Pro Lys Asp Ser Thr Leu Leu Arg Asp
                725                 730                 735

His Glu Ile Arg Ala Ser Leu Thr Lys His Phe Gly Leu Leu Glu Thr
            740                 745                 750

Ala Leu Glu Glu Glu Asp Leu Ala Ser Cys Lys Ser Pro Glu Tyr Asp
        755                 760                 765

Thr Val Phe Glu Asp Ser Ser Ser Ser Gly Glu Ser Ser Phe Leu
770                 775                 780

Pro Glu Glu Glu Glu Glu Gly Glu Glu Glu Glu Asp Asp Glu
785                 790                 795                 800

Glu Glu Asp Ser Gly Val Ser Pro Thr Cys Ser Asp His Cys Pro Tyr
                805                 810                 815

Gln Ser Pro Pro Ser Lys Ala Asn Arg Gln Leu Cys Ser Arg Ser Arg
            820                 825                 830

Ser Ser Ser Gly Ser Ser Pro Cys His Ser Trp Ser Pro Ala Thr Arg
        835                 840                 845

Arg Asn Phe Arg Cys Glu Ser Arg Gly Pro Cys Ser Asp Arg Thr Pro
850                 855                 860

Ser Ile Arg His Ala Arg Lys Arg Glu Lys Ala Ile Gly Glu Gly
865                 870                 875                 880

Arg Val Val Tyr Ile Gln Asn Leu Ser Ser Asp Met Ser Ser Arg Glu
                885                 890                 895

Leu Lys Arg Arg Phe Glu Val Phe Gly Glu Ile Glu Glu Cys Glu Val
            900                 905                 910

Leu Thr Arg Asn Arg Arg Gly Glu Lys Tyr Gly Phe Ile Thr Tyr Arg
        915                 920                 925

Cys Ser Glu His Ala Ala Leu Ser Leu Thr Lys Gly Ala Ala Leu Arg
930                 935                 940

Lys Arg Asn Glu Pro Ser Phe Gln Leu Ser Tyr Gly Gly Leu Arg His
945                 950                 955                 960

Phe Cys Trp Pro Arg Tyr Thr Asp Tyr Gly Lys Pro Leu Lys Pro Ser
                965                 970                 975

His Ser Leu Val Arg Leu Lys Ala Trp Glu Ala Val Pro Ser Leu Asn
            980                 985                 990

Lys Thr Gln Ser
        995

<210> SEQ ID NO 5
<211> LENGTH: 1496
<212> TYPE: DNA
```

<213> ORGANISM: Homo sapiens

<400> SEQUENCE: 5

| | | | | | |
|---|---|---|---|---|---|
| gtcacaaagc | gacccaactt | ttggcaagaa | gagctttgag | cagaccttga | cagtggagct | 60 |
| ctgtggcaca | gcaggactca | ccccacccac | cacaccaccg | tacaagccca | cagaggagga | 120 |
| tcccttcaaa | ccagacatca | agcatagtct | aggcaaagaa | atagctctca | gcctcccctc | 180 |
| ccctgagggc | ctctcactca | aggccacccc | agggctgcc | cacaagctgc | caaagaagca | 240 |
| cccagagcga | agtgagctcc | tgtcccacct | gcgacatgcc | acagcccagc | cagcctccca | 300 |
| ggctggccag | aagcgtccct | tctcctgttc | ctttggagac | catgactact | gccaggtgct | 360 |
| ccgaccagaa | ggcgtcctgc | aaaggaaggt | gctgaggtcc | tgggagccgt | ctggggttca | 420 |
| ccttgaggac | tggccccagc | agggtgcccc | ttgggctgag | gcacaggccc | ctggcaggga | 480 |
| ggaagacaga | agctgtgatg | ctggcgcccc | acccaaggac | agcacgctgc | tgagagacca | 540 |
| tgagatccgt | gccagcctca | ccaaacactt | tgggctgctg | gagaccgccc | tggaggagga | 600 |
| agacctggcc | tcctgcaaga | gccctgagta | tgacactgtc | tttgaagaca | gcagcagcag | 660 |
| cagcggcgag | agcagcttcc | tcccagagga | ggaagaggaa | gaggggagg | aggaggagga | 720 |
| ggacgatgaa | gaagaggact | caggggtcag | ccccacttgc | tctgaccact | gccctacca | 780 |
| gagcccacca | agcaaggcca | accggcagct | ctgttcccgc | agccgctcaa | gctctggctc | 840 |
| ttcaccctgc | cactcctggt | caccagccac | tcgaaggaac | ttcagcagat | gtgagagcag | 900 |
| agggccgtgt | tcagacagaa | cgccaagcat | ccggcacgcc | aggaagcggc | gggaaaaggc | 960 |
| cattggggaa | ggccgcgtgg | tgtacattca | aaatctctcc | agcgacatga | gctcccgaga | 1020 |
| gctgaagagg | cgctttgaag | tgtttggtga | gattgaggag | tgcgaggtgc | tgacaagaaa | 1080 |
| taggagaggc | gagaagtacg | gcttcatcac | ctaccggtgt | tctgagcacg | cggccctctc | 1140 |
| tttgacaaag | ggcgctgccc | tgaggaagcg | caacgagccc | tccttccagc | tgagctacgg | 1200 |
| agggctccgg | cacttctgct | ggcccagata | cactgactac | gattccaatt | cagaagaggc | 1260 |
| ccttcctgcg | tcagggaaaa | gcaagtatga | agccatggat | tttgcagct | tactgaaaga | 1320 |
| ggcccagcag | agcctgcatt | gataacagcc | ttaaccctcg | aggaatacct | caatacctca | 1380 |
| gacaaggccc | ttccaatatg | tttacgtttt | caaagaaatc | aagtatatga | ggagagcgag | 1440 |
| cgagcgtgag | agaacacccg | tgagagagac | ttgaaactgc | tgtcctaaaa | aaaaaa | 1496 |

<210> SEQ ID NO 6
<211> LENGTH: 172
<212> TYPE: DNA
<213> ORGANISM: Homo sapiens

<400> SEQUENCE: 6

| | | | | | |
|---|---|---|---|---|---|
| actccgccgc | acgctgcagc | cgcggctgga | agatggcggg | gaacgactgc | ggcgcgctgc | 60 |
| tggacgaaga | gctctcctcc | ttcttcctca | actatctcgc | tgacacgcag | ggtggagggt | 120 |
| ccggggagga | gcaactctat | gctgactttc | agaacttga | cctctcccag | ct | 172 |

<210> SEQ ID NO 7
<211> LENGTH: 3267
<212> TYPE: DNA
<213> ORGANISM: Homo sapiens

<400> SEQUENCE: 7

| | | | | | |
|---|---|---|---|---|---|
| actccgccgc | acgctgcagc | cgcggctgga | agatggcggg | gaacgactgc | ggcgcgctgc | 60 |
| tggacgaaga | gctctcctcc | ttcttcctca | actatctcgc | tgacacgcag | ggtggagggt | 120 |

-continued

```
ccggggagga gcaactctat gctgactttc cagaacttga cctctcccag ctggatgcca    180
gcgactttga ctcggccacc tgctttgggg agctgcagtg gtgcccagag aactcagaga    240
ctgaacccaa ccagtacagc cccgatgact ccgagctctt ccagattgac agtgagaatg    300
aggccctcct ggcagagctc accaagaccc tggatgacat ccctgaagat gacgtgggtc    360
tggctgcctt cccagccctg gatggtggag acgctctatc atgcacctca gcttcgcctg    420 cccctcatc tgcacccccc agccctgccc cggagaagcc ctcggcccca gcccctgagg     480
tggacgagct ctcactgctg cagaagctcc tcctggccac atcctaccca acatcaagct    540
ctgacaccca gaaggaaggg accgcctggc gccaggcagg cctcagatct aaaagtcaac    600
ggccttgtgt taaggcggac agcacccaag acaagaaggc tcccatgatg cagtctcaga    660
gccgaagttg tacagaacta cataagcacc tcacctcggc acagtgctgc ctgcaggatc    720
ggggtctgca gccaccatgc ctccagagtc ccggctccc tgccaaggag acaaggagc     780 cgggtgagga ctgcccgagc cccagccag ctccagcctc tccccaggac tccctagctc     840
tgggcagggc agaccccggt gccccggttt ccaggaaga catgcaggcg atggtgcaac    900
tcatacgcta catgcacacc tactgcctcc cccagaggaa gctgccccca cagacccctg    960
agccactccc caaggcctgc agcaacccct cccagcaggt cagatcccgg ccctggtccc   1020
ggcaccactc caaagcctcc tgggctgagt tctccattct gagggaactt ctggctcaag   1080
acgtgctctg tgatgtcagc aaaccctacc gtctggccac gcctgtttat gcctccctca   1140
cacctcggtc aaggcccagg cccccaaag acagtcaggc ctcccctggt cgcccgtcct    1200
cggtggagga ggtaaggatc gcagcttcac ccaagagcac cgggcccaga ccaagcctgc   1260
gcccactgcg gctggaggtg aaaagggagg tccgccggcc tgccagactg cagcagcagg   1320
aggaggaaga cgaggaagaa gaggaggagg aagaggaaga agaaaaagag gaggaggagg   1380 agtgggcag aaaaggcca ggccgaggcc tgccatggac gaagctgggg aggaagctgg     1440
agagctctgt gtgccccgtg cggcgttctc ggagactgaa ccctgagctg gcccctggc   1500 tgacatttgc agatgagccg ctggtcccct cggagcccca aggtgctctg ccctcactgt   1560
gcctggctcc caaggcctac gacgtagagc gggagctggg cagccccacg gacgaggaca   1620
gtggccaaga ccagcagctc ctacggggac cccagatccc tgccctggag agccctgtg    1680 agagtgggtg tggggacatg gatgaggacc ccagctgccc gcagctccct cccagagact   1740
ctcccaggtg cctcatgctg gccttgtcac aaagcgaccc aacttttggc aagaagagct   1800
ttgagcagac cttgacagtg gagctctgtg gcacagcagg actcaccccca cccaccacac   1860 caccgtacaa gccacagag gaggatccct tcaaaccaga catcaagcat agtctaggca    1920
aagaaatagc tctcagcctc ccctcccctg agggcctctc actcaaggcc accccagggg   1980
ctgcccacaa gctgccaaag aagcacccag agcgaagtga gctcctgtcc cacctgcgac   2040
atgccacagc ccagccagcc tcccaggctg gccagaagcg tcccttctcc tgttcctttg   2100
gagaccatga ctactgccag gtgctccgac cagaaggcgt cctgcaaagg aaggtgctga   2160
ggtcctggga gccgtctggg gttcacctttg aggactggcc ccagcagggt gcccccttggg  2220 ctgaggcaca ggcccctggc agggaggaag acagaagctg tgatgctggt gccccaccca   2280
aggacagcac gctgctgaga gaccatgaga tccgtgctag cctcaccaaa cactttgggc   2340
tgctggagac cgccctggag gaggaagacc tggcctcctg caagagccct gagtatgaca   2400
ctgtctttga agacagcagc agcagcagcg gcgagagcag cttcctccca gaggaggaag   2460
```

-continued

```
aggaagaagg ggaggaggag gaggaggacg atgaagaaga ggactcaggg gtcagcccca      2520
cttgctctga ccactgcccc taccagagcc caccaagcaa ggccaaccgg cagctctgtt      2580
cccgcagccg ctcaagctct ggctcttcac cctgccactc ctggtcacca gccactcgaa      2640
ggaacttcag atgtgagagc agagggccgt gttcagacag aacgccaagc atccggcacg      2700
ccaggaagcg gcgggaaaag gccattgggg aaggccgcgt ggtgtacatt caaaatctct      2760
ccagcgacat gagctcccga gagctgaaga ggcgctttga agtgtttggt gagattgagg      2820
agtgcgaggt gctgacaaga aataggagag gcgagaagta cggcttcatc acctaccggt      2880
gttctgagca cgcggccctc tctttgacaa agggcgctgc cctgaggaag cgcaacgagc      2940
cctccttcca gctgagctac ggagggctcc ggcacttctg ctggcccaga tacactgact      3000
acgattccaa ttcagaagag gcccttcctg cgtcagggaa aagcaagtat gaagccatgg      3060
attttgacag cttactgaaa gaggcccagc agagcctgca ttgataacag ccttaaccct      3120
cgaggaatac ctcaatacct cagacaaggc ccttccaata tgtttacgtt ttcaaagaaa      3180
tcaagtatat gaggagagcg agcgagcgtg agagaacacc cgtgagagag acttgaaact      3240
gctgtccttt aaaaaaaaaa aaaaaaa                                         3267
```

<210> SEQ ID NO 8
<211> LENGTH: 1023
<212> TYPE: PRT
<213> ORGANISM: Homo sapiens

<400> SEQUENCE: 8

```
Met Ala Gly Asn Asp Cys Gly Ala Leu Leu Asp Glu Glu Leu Ser Ser
1               5                   10                  15

Phe Phe Leu Asn Tyr Leu Ala Asp Thr Gln Gly Gly Ser Gly Glu
            20                  25                  30

Glu Gln Leu Tyr Ala Asp Phe Pro Glu Leu Asp Leu Ser Gln Leu Asp
        35                  40                  45

Ala Ser Asp Phe Asp Ser Ala Thr Cys Phe Gly Glu Leu Gln Trp Cys
    50                  55                  60

Pro Glu Asn Ser Glu Thr Glu Pro Asn Gln Tyr Ser Pro Asp Asp Ser
65                  70                  75                  80

Glu Leu Phe Gln Ile Asp Ser Glu Asn Glu Ala Leu Leu Ala Glu Leu
                85                  90                  95

Thr Lys Thr Leu Asp Asp Ile Pro Glu Asp Asp Val Gly Leu Ala Ala
            100                 105                 110

Phe Pro Ala Leu Asp Gly Gly Asp Ala Leu Ser Cys Thr Ser Ala Ser
        115                 120                 125

Pro Ala Pro Ser Ser Ala Pro Ser Pro Ala Pro Glu Lys Pro Ser
    130                 135                 140

Ala Pro Ala Pro Glu Val Asp Glu Leu Ser Leu Leu Gln Lys Leu Leu
145                 150                 155                 160

Leu Ala Thr Ser Tyr Pro Thr Ser Ser Asp Thr Gln Lys Glu Gly
                165                 170                 175

Thr Ala Trp Arg Gln Ala Gly Leu Arg Ser Lys Ser Gln Arg Pro Cys
            180                 185                 190

Val Lys Ala Asp Ser Thr Gln Asp Lys Lys Ala Pro Met Met Gln Ser
        195                 200                 205

Gln Ser Arg Ser Cys Thr Glu Leu His Lys His Leu Thr Ser Ala Gln
    210                 215                 220

Cys Cys Leu Gln Asp Arg Gly Leu Gln Pro Pro Cys Leu Gln Ser Pro
```

-continued

```
            225                 230                 235                 240

Arg Leu Pro Ala Lys Glu Asp Lys Glu Pro Gly Glu Asp Cys Pro Ser
                245                 250                 255

Pro Gln Pro Ala Pro Ala Ser Pro Gln Asp Ser Leu Ala Leu Gly Arg
                260                 265                 270

Ala Asp Pro Gly Ala Pro Val Ser Gln Glu Asp Met Gln Ala Met Val
                275                 280                 285

Gln Leu Ile Arg Tyr Met His Thr Tyr Cys Leu Pro Gln Arg Lys Leu
            290                 295                 300

Pro Pro Gln Thr Pro Glu Pro Leu Pro Lys Ala Cys Ser Asn Pro Ser
305                 310                 315                 320

Gln Gln Val Arg Ser Arg Pro Trp Ser Arg His Ser Lys Ala Ser
                325                 330                 335

Trp Ala Glu Phe Ser Ile Leu Arg Glu Leu Leu Ala Gln Asp Val Leu
                340                 345                 350

Cys Asp Val Ser Lys Pro Tyr Arg Leu Ala Thr Pro Val Tyr Ala Ser
                355                 360                 365

Leu Thr Pro Arg Ser Arg Pro Arg Pro Lys Asp Ser Gln Ala Ser
            370                 375                 380

Pro Gly Arg Pro Ser Ser Val Glu Val Arg Ile Ala Ala Ser Pro
385                 390                 395                 400

Lys Ser Thr Gly Pro Arg Pro Ser Leu Arg Pro Leu Arg Leu Glu Val
                405                 410                 415

Lys Arg Glu Val Arg Arg Pro Ala Arg Leu Gln Gln Gln Glu Glu Glu
                420                 425                 430

Asp Glu Glu Glu Glu Glu Glu Glu Glu Glu Lys Glu Glu Glu
            435                 440                 445

Glu Glu Trp Gly Arg Lys Arg Pro Gly Arg Gly Leu Pro Trp Thr Lys
            450                 455                 460

Leu Gly Arg Lys Leu Glu Ser Ser Val Cys Pro Val Arg Arg Ser Arg
465                 470                 475                 480

Arg Leu Asn Pro Glu Leu Gly Pro Trp Leu Thr Phe Ala Asp Glu Pro
                485                 490                 495

Leu Val Pro Ser Glu Pro Gln Gly Ala Leu Pro Ser Leu Cys Leu Ala
                500                 505                 510

Pro Lys Ala Tyr Asp Val Glu Arg Glu Leu Gly Ser Pro Thr Asp Glu
                515                 520                 525

Asp Ser Gly Gln Asp Gln Leu Leu Arg Gly Pro Gln Ile Pro Ala
                530                 535                 540

Leu Glu Ser Pro Cys Glu Ser Gly Cys Gly Asp Met Asp Glu Asp Pro
545                 550                 555                 560

Ser Cys Pro Gln Leu Pro Pro Arg Asp Ser Pro Arg Cys Leu Met Leu
                565                 570                 575

Ala Leu Ser Gln Ser Asp Pro Thr Phe Gly Lys Lys Ser Phe Glu Gln
                580                 585                 590

Thr Leu Thr Val Glu Leu Cys Gly Thr Ala Gly Leu Thr Pro Thr
                595                 600                 605

Thr Pro Pro Tyr Lys Pro Thr Glu Glu Asp Pro Phe Lys Pro Asp Ile
                610                 615                 620

Lys His Ser Leu Gly Lys Glu Ile Ala Leu Ser Leu Pro Ser Pro Glu
625                 630                 635                 640

Gly Leu Ser Leu Lys Ala Thr Pro Gly Ala Ala His Lys Leu Pro Lys
                645                 650                 655
```

-continued

Lys His Pro Glu Arg Ser Glu Leu Leu Ser His Leu Arg His Ala Thr
        660                 665                 670

Ala Gln Pro Ala Ser Gln Ala Gly Gln Lys Arg Pro Phe Ser Cys Ser
        675                 680                 685

Phe Gly Asp His Asp Tyr Cys Gln Val Leu Arg Pro Glu Gly Val Leu
        690                 695                 700

Gln Arg Lys Val Leu Arg Ser Trp Glu Pro Ser Gly Val His Leu Glu
705                 710                 715                 720

Asp Trp Pro Gln Gln Gly Ala Pro Trp Ala Glu Ala Gln Ala Pro Gly
                725                 730                 735

Arg Glu Glu Asp Arg Ser Cys Asp Ala Gly Ala Pro Lys Asp Ser
        740                 745                 750

Thr Leu Leu Arg Asp His Glu Ile Arg Ala Ser Leu Thr Lys His Phe
        755                 760                 765

Gly Leu Leu Glu Thr Ala Leu Glu Glu Glu Asp Leu Ala Ser Cys Lys
770                 775                 780

Ser Pro Glu Tyr Asp Thr Val Phe Glu Asp Ser Ser Ser Ser Gly
785                 790                 795                 800

Glu Ser Ser Phe Leu Pro Glu Glu Glu Glu Gly Glu Glu Glu
                805                 810                 815

Glu Glu Asp Asp Glu Glu Asp Ser Gly Val Ser Pro Thr Cys Ser
            820                 825                 830

Asp His Cys Pro Tyr Gln Ser Pro Ser Lys Ala Asn Arg Gln Leu
        835                 840                 845

Cys Ser Arg Ser Arg Ser Ser Gly Ser Ser Pro Cys His Ser Trp
        850                 855                 860

Ser Pro Ala Thr Arg Arg Asn Phe Arg Cys Glu Ser Arg Gly Pro Cys
865                 870                 875                 880

Ser Asp Arg Thr Pro Ser Ile Arg His Ala Arg Lys Arg Glu Lys
                885                 890                 895

Ala Ile Gly Glu Gly Arg Val Val Tyr Ile Gln Asn Leu Ser Ser Asp
        900                 905                 910

Met Ser Ser Arg Glu Leu Lys Arg Arg Phe Glu Val Phe Gly Glu Ile
        915                 920                 925

Glu Glu Cys Glu Val Leu Thr Arg Asn Arg Arg Gly Glu Lys Tyr Gly
        930                 935                 940

Phe Ile Thr Tyr Arg Cys Ser Glu His Ala Ala Leu Ser Leu Thr Lys
945                 950                 955                 960

Gly Ala Ala Leu Arg Lys Arg Asn Glu Pro Ser Phe Gln Leu Ser Tyr
                965                 970                 975

Gly Gly Leu Arg His Phe Cys Trp Pro Arg Tyr Thr Asp Tyr Ser
        980                 985                 990

Asn Ser Glu Glu Ala Leu Pro Ala Ser Gly Lys Ser Lys Tyr Glu Ala
        995                 1000                1005

Met Asp Phe Asp Ser Leu Leu Lys Glu Ala Gln Gln Ser Leu His
        1010                1015                1020

<210> SEQ ID NO 9
<211> LENGTH: 3163
<212> TYPE: DNA
<213> ORGANISM: Rattus norvegicus

<400> SEQUENCE: 9 atgcagggggg aagggaaggg tggggagtct ggagaggaac agttatgtgc tgacttgcca     60

-continued

```
gagctcgacc tctcccagct ggatgccagt gacttcgact cagccacgtg ctttggggag      120
ctgcagtggt gcccggagac ctcagagaca gagcccagcc agtacagccc tgatgattcc      180
gagttcttcc agattgacag tgagaatgaa gctctcttgg ctgcgcttac caagaccctg      240
gatgacatcc ccgaagacga tgtgggggctg gctgccttcc aggactgga tgaaggcgac      300 acacctcct gcaccccagc ttacctgct cctttatctg tgcccccag ccccgccttg         360 gagaggcttc tgtcccagt gtctgaagtg gatgagcttt cactgctgca gaagctcctc       420
ctggccacat cctccccaac agcaagctct gatgctctga aggacggggc cacctggtcg      480
cagaccagcc tcagttccag aagtcagcgg ccttgtgtca aggtggatgg cacccaggac     540
aagaagaccc ccatgctacg gtctcagagc cggccttgta cagaactgca taagcacctc     600
acttcggtgc tgccctgccc caggggaaaa gcctgttccc cacctcccca cccaagtcct    660
cagctcctct ccaaagagga tgaggaggtg ggagaggatt gcccaagccc ctggccagct    720
ccagcgtctc cccaagactc actaggacag gacacggcca accccaacag tgcccaagtt     780
cccaaggacg acgtgagggc catggtacag ctcattcgct acatgcatac ctactgcctg    840
cctcagagga agctgcccca cgggcctca gagccaatcc cccagtcctg cagcagcccc     900
ttgaggaagg tcccaccccg atcccggcaa acccccaaag ccttctggac tgagttctcc    960
atcctaaggg aacttctggc caagatatc ctctgtgatg ttagcaagcc ctaccgcctg     1020
gccacacctg tctatgcttc tctcacaccc cagtccagaa ccaggccccc caaagacagt    1080
caggcctccc ctgcccactc tgccatggca gaagaggtga gaatcactgc ttcccccaag    1140
agcactggac ctagacccag cctccgtcct ctgaggctag aggtgaaacg ggatgtcaac    1200
aagcctgcaa ggcaaaagcg ggaggaagat gaggaggagg aagaggaaga agaagaggaa    1260
gaagaaaaag aggatgaaga agaggagtgg ggcaggaaga gaccaggtcg tggcctgcca    1320
tggaccaaac tagggaggaa gatggacagc tctgtgtgcc ctgtgcggcg ctccaggaga    1380
ctgaatccag agctgggccc ttggctgaca ttcactgatg agcccctagg tgctctaccc    1440
tcgatgtgcc tggctacaga gacccacgac ctggaagaag agctgggcgg cctcacagac    1500
agtagtcaag gccagcagct cccccctggga tcccagatcc ccaccctgga aagcccctgt    1560
gaaagtgggt gtggggacac agatgaagat ccaagctgcc cgcggccccc ttccagagac    1620
tcccccaggt gcctcatgct ggccttgtca caaagtgacc ctcttggcaa gaagagcttt    1680
gaggagtcct tgacagtgga gctttgtggc acagcaggac tcactccacc caccacacct    1740
ccatataagc ccatggagga ggaccccttc aagcaggaca ccaagcacag cccaggccaa    1800
gacacagctc ccagcctccc ttcccctgag actcttcagc tcacagccac cccaggggct    1860
tcccacaagc tgcccaagag gcacccggag cgaagtgagc tcctgtctca tctgcaacat    1920
gccacaaccc agccagtctc acaggctggc cagaagcgtc ccttctcctg ctccttttgga    1980 gaccatgact actgccaggt gatcaggcca gaggctgccc tgcagaggaa ggtgctgcgg    2040
tcctgggagc caatcaaggt ccaccttgaa gacttggccc accagggtgc aaccctgcca    2100
gtggaaacaa agaccccctag gagggaggca gaccagaact gtgaccccac ccccaaggac    2160
agcatgcagc taagagacca tgagatccgt gccagcctca caaagcactt tgggctgctg    2220
gaaaccgctc tggaggagga agacttggct tcatgtaaaa gcccggagta tgacaccgta    2280
tttgaggaca gcagcagcag cagtggcgag agcagcttcc tgctagagga ggaggaagag    2340
gagggagggg aagaggacga tgaaggagag gactcagggg tcagccctcc ctgctccgac    2400
```

-continued

```
cactgcccct accagagccc acccagtaag gccagtcggc agctctgttc ccgaagccgc    2460
tccagttctg gctcctcatc ctgtagctcc tggtcaccag ctacccggaa gaacttcaga    2520
cttgagagca gagggccctg ttcagatgga accccaagcg cccggcatgc caagaagcgg    2580
cgggaaaagg ccatcggtga aggtcgtgtg gtatacatcc gaaatctctc cggtgacatg    2640
agctctcgag aactaaagaa gcgcttcgag gtgtttggtg agatagtcga gtgccaggtg    2700
ctgaggagaa gtaagagagg ccagaagcac ggttttatta ccttccggtg ttcggagcat    2760
gccgccctgt ccgtgaggaa cggcgctacc ctgagaaaac gcaatgagcc ctccttccac    2820
ctgagctatg gagggctccg gcacttccgc tggcccagat acaccgacta tgatcccacg    2880
tctgaagagt cccttccctc gtctgggaaa agcaagtacg aagccatgga ttttgacagc    2940
ttactgaaag aggcccagca gagcctgcat taatatcagc cttaaccttc gaggaatacc    3000 tcaataccte agacaaggcc cttccaatat gtttacgttt tcaaagaaat gagtatatga    3060
ggaggagagc aagccaatga gcgagcgagc gagcgagcgt gagagaacac acaggagaga    3120
gagacttgaa tctgctgtcg tttcctttaa aaaaaaaaaa aaa                      3163
```

<210> SEQ ID NO 10
<211> LENGTH: 990
<212> TYPE: PRT
<213> ORGANISM: Rattus norvegicus

<400> SEQUENCE: 10

```
Met Gln Gly Glu Gly Lys Gly Gly Glu Ser Gly Glu Glu Gln Leu Cys
1               5                   10                  15

Ala Asp Leu Pro Glu Leu Asp Leu Ser Gln Leu Asp Ala Ser Asp Phe
            20                  25                  30

Asp Ser Ala Thr Cys Phe Gly Glu Leu Gln Trp Cys Pro Glu Thr Ser
        35                  40                  45

Glu Thr Glu Pro Ser Gln Tyr Ser Pro Asp Asp Ser Glu Phe Phe Gln
    50                  55                  60

Ile Asp Ser Glu Asn Glu Ala Leu Leu Ala Ala Leu Thr Lys Thr Leu
65                  70                  75                  80

Asp Asp Ile Pro Glu Asp Asp Val Gly Leu Ala Ala Phe Pro Gly Leu
                85                  90                  95

Asp Glu Gly Asp Thr Pro Ser Cys Thr Pro Ala Ser Pro Ala Pro Leu
            100                 105                 110

Ser Val Pro Pro Ser Pro Ala Leu Glu Arg Leu Leu Ser Pro Val Ser
        115                 120                 125

Glu Val Asp Glu Leu Ser Leu Leu Gln Lys Leu Leu Leu Ala Thr Ser
    130                 135                 140

Ser Pro Thr Ala Ser Ser Asp Ala Leu Lys Asp Gly Ala Thr Trp Ser
145                 150                 155                 160

Gln Thr Ser Leu Ser Ser Arg Ser Gln Arg Pro Cys Val Lys Val Asp
                165                 170                 175

Gly Thr Gln Asp Lys Lys Thr Pro Met Leu Arg Ser Gln Ser Arg Pro
            180                 185                 190

Cys Thr Glu Leu His Lys His Leu Thr Ser Val Leu Pro Cys Pro Arg
        195                 200                 205

Gly Lys Ala Cys Ser Pro Pro His Pro Ser Pro Gln Leu Leu Ser
    210                 215                 220

Lys Glu Asp Glu Glu Val Gly Glu Asp Cys Pro Ser Pro Trp Pro Ala
225                 230                 235                 240
```

-continued

```
Pro Ala Ser Pro Gln Asp Ser Leu Gly Gln Asp Thr Ala Asn Pro Asn
            245                 250                 255

Ser Ala Gln Val Pro Lys Asp Asp Val Arg Ala Met Val Gln Leu Ile
        260                 265                 270

Arg Tyr Met His Thr Tyr Cys Leu Pro Gln Arg Lys Leu Pro Gln Arg
    275                 280                 285

Ala Ser Glu Pro Ile Pro Gln Ser Cys Ser Ser Pro Leu Arg Lys Val
290                 295                 300

Pro Pro Arg Ser Arg Gln Thr Pro Lys Ala Phe Trp Thr Glu Phe Ser
305                 310                 315                 320

Ile Leu Arg Glu Leu Leu Ala Gln Asp Ile Leu Cys Asp Val Ser Lys
                325                 330                 335

Pro Tyr Arg Leu Ala Thr Pro Val Tyr Ala Ser Leu Thr Pro Gln Ser
            340                 345                 350

Arg Thr Arg Pro Pro Lys Asp Ser Gln Ala Ser Pro Ala His Ser Ala
        355                 360                 365

Met Ala Glu Glu Val Arg Ile Thr Ala Ser Pro Lys Ser Thr Gly Pro
    370                 375                 380

Arg Pro Ser Leu Arg Pro Leu Arg Leu Glu Val Lys Arg Asp Val Asn
385                 390                 395                 400

Lys Pro Ala Arg Gln Lys Arg Glu Glu Asp Glu Glu Glu Glu Glu Glu
                405                 410                 415

Glu Glu Glu Glu Glu Lys Glu Asp Glu Glu Glu Trp Gly Arg
            420                 425                 430

Lys Arg Pro Gly Arg Gly Leu Pro Trp Thr Lys Leu Gly Arg Lys Met
        435                 440                 445

Asp Ser Ser Val Cys Pro Val Arg Arg Ser Arg Arg Leu Asn Pro Glu
    450                 455                 460

Leu Gly Pro Trp Leu Thr Phe Thr Asp Glu Pro Leu Gly Ala Leu Pro
465                 470                 475                 480

Ser Met Cys Leu Ala Thr Glu Thr His Asp Leu Glu Glu Glu Leu Gly
                485                 490                 495

Gly Leu Thr Asp Ser Ser Gln Gly Gln Gln Leu Pro Leu Gly Ser Gln
            500                 505                 510

Ile Pro Thr Leu Glu Ser Pro Cys Glu Ser Gly Cys Gly Asp Thr Asp
        515                 520                 525

Glu Asp Pro Ser Cys Pro Arg Pro Pro Ser Arg Asp Ser Pro Arg Cys
    530                 535                 540

Leu Met Leu Ala Leu Ser Gln Ser Asp Pro Leu Gly Lys Lys Ser Phe
545                 550                 555                 560

Glu Glu Ser Leu Thr Val Glu Leu Cys Gly Thr Ala Gly Leu Thr Pro
                565                 570                 575

Pro Thr Thr Pro Pro Tyr Lys Pro Met Glu Glu Asp Pro Phe Lys Gln
            580                 585                 590

Asp Thr Lys His Ser Pro Gly Gln Asp Thr Ala Pro Ser Leu Pro Ser
        595                 600                 605

Pro Glu Thr Leu Gln Leu Thr Ala Thr Pro Gly Ala Ser His Lys Leu
    610                 615                 620

Pro Lys Arg His Pro Glu Arg Ser Glu Leu Leu Ser His Leu Gln His
625                 630                 635                 640

Ala Thr Thr Gln Pro Val Ser Gln Ala Gly Gln Lys Arg Pro Phe Ser
                645                 650                 655

Cys Ser Phe Gly Asp His Asp Tyr Cys Gln Val Ile Arg Pro Glu Ala
```

```
                    660             665             670
    Ala Leu Gln Arg Lys Val Leu Arg Ser Trp Glu Pro Ile Lys Val His
                675             680             685

Leu Glu Asp Leu Ala His Gln Gly Ala Thr Leu Pro Val Glu Thr Lys
                690             695             700

Thr Pro Arg Arg Glu Ala Asp Gln Asn Cys Asp Pro Thr Pro Lys Asp
    705             710             715             720

Ser Met Gln Leu Arg Asp His Glu Ile Arg Ala Ser Leu Thr Lys His
                        725             730             735

Phe Gly Leu Leu Glu Thr Ala Leu Glu Glu Asp Leu Ala Ser Cys
                740             745             750

Lys Ser Pro Glu Tyr Asp Thr Val Phe Glu Asp Ser Ser Ser Ser
                755             760             765

Gly Glu Ser Ser Phe Leu Leu Glu Glu Glu Glu Glu Gly Gly Glu
                770             775             780

Glu Asp Asp Glu Gly Glu Asp Ser Gly Val Ser Pro Cys Ser Asp
    785             790             795             800

His Cys Pro Tyr Gln Ser Pro Ser Lys Ala Ser Arg Gln Leu Cys
                    805             810             815

Ser Arg Ser Arg Ser Ser Gly Ser Ser Cys Ser Ser Trp Ser
                820             825             830

Pro Ala Thr Arg Lys Asn Phe Arg Leu Glu Ser Arg Gly Pro Cys Ser
                835             840             845

Asp Gly Thr Pro Ser Ala Arg His Ala Lys Arg Glu Lys Ala
    850             855             860

Ile Gly Glu Gly Arg Val Val Tyr Ile Arg Asn Leu Ser Gly Asp Met
    865             870             875             880

Ser Ser Arg Glu Leu Lys Lys Arg Phe Glu Val Phe Gly Glu Ile Val
                885             890             895

Glu Cys Gln Val Leu Arg Arg Ser Arg Gly Gln Lys His Gly Phe
                900             905             910

Ile Thr Phe Arg Cys Ser Glu His Ala Ala Leu Ser Val Arg Asn Gly
                915             920             925

Ala Thr Leu Arg Lys Arg Asn Glu Pro Ser Phe His Leu Ser Tyr Gly
                930             935             940

Gly Leu Arg His Phe Arg Trp Pro Arg Tyr Thr Asp Tyr Asp Pro Thr
    945             950             955             960

Ser Glu Glu Ser Leu Pro Ser Ser Gly Lys Ser Lys Tyr Glu Ala Met
                    965             970             975

Asp Phe Asp Ser Leu Leu Lys Glu Ala Gln Gln Ser Leu His
                980             985             990

<210> SEQ ID NO 11
<211> LENGTH: 20
<212> TYPE: DNA
<213> ORGANISM: Artificial Sequence
<220> FEATURE:
<223> OTHER INFORMATION: forward primer CME 9748

<400> SEQUENCE: 11
gtcacaaagc gacccaactt                                          20

<210> SEQ ID NO 12
<211> LENGTH: 22
<212> TYPE: DNA
<213> ORGANISM: Artificial Sequence
```

-continued

```
<220> FEATURE:
<223> OTHER INFORMATION: reverse primer CME 9749

<400> SEQUENCE: 12
gagtcatggt ctccaaagga ac                                              22

<210> SEQ ID NO 13
<211> LENGTH: 27
<212> TYPE: DNA
<213> ORGANISM: Artificial Sequence
<220> FEATURE:
<223> OTHER INFORMATION: AP1 adaptor primer

<400> SEQUENCE: 13
ccatcctaat acgactcact atagggc                                         27

<210> SEQ ID NO 14
<211> LENGTH: 22
<212> TYPE: DNA
<213> ORGANISM: Artificial Sequence
<220> FEATURE:
<223> OTHER INFORMATION: CME 9830 forward primer

<400> SEQUENCE: 14
gccactcgaa ggaacttcag at                                              22

<210> SEQ ID NO 15
<211> LENGTH: 22
<212> TYPE: DNA
<213> ORGANISM: Artificial Sequence
<220> FEATURE:
<223> OTHER INFORMATION: CME 9850 reverse primer B

<400> SEQUENCE: 15
gggttaaggc tgttatcaat gc                                              22

<210> SEQ ID NO 16
<211> LENGTH: 22
<212> TYPE: DNA
<213> ORGANISM: Artificial Sequence
<220> FEATURE:
<223> OTHER INFORMATION: CME 9831 reverse primer A

<400> SEQUENCE: 16
aggccagaag agaaacagga tg                                              22

<210> SEQ ID NO 17
<211> LENGTH: 22
<212> TYPE: DNA
<213> ORGANISM: Artificial Sequence
<220> FEATURE:
<223> OTHER INFORMATION: CME 9726 sequencing primer

<400> SEQUENCE: 17
cttctcctgt tcctttggag ac                                              22

<210> SEQ ID NO 18
<211> LENGTH: 20
<212> TYPE: DNA
<213> ORGANISM: Artificial Sequence
<220> FEATURE:
<223> OTHER INFORMATION: CME 9727 sequencing primer

<400> SEQUENCE: 18
tggggttcac ttgaggattg                                                 20
```

<210> SEQ ID NO 19
<211> LENGTH: 22
<212> TYPE: DNA
<213> ORGANISM: Artificial Sequence
<220> FEATURE:
<223> OTHER INFORMATION: CME 9778 sequencing primer

<400> SEQUENCE: 19
attcaaaatc tcttccagcg ac                                              22

<210> SEQ ID NO 20
<211> LENGTH: 22
<212> TYPE: DNA
<213> ORGANISM: Artificial Sequence
<220> FEATURE:
<223> OTHER INFORMATION: CME 9776 sequencing primer

<400> SEQUENCE: 20
gaagacagaa gctgtgatgc tg                                              22

<210> SEQ ID NO 21
<211> LENGTH: 21
<212> TYPE: DNA
<213> ORGANISM: Artificial SEquence
<220> FEATURE:
<223> OTHER INFORMATION: SP1A primer

<400> SEQUENCE: 21
catcacagag cacgtcttga g                                               21

<210> SEQ ID NO 22
<211> LENGTH: 25
<212> TYPE: DNA
<213> ORGANISM: Artificial Sequence
<220> FEATURE:
<223> OTHER INFORMATION: SP2A primer

<400> SEQUENCE: 22
catgtagcgt atgagttgca ccatc                                           25

<210> SEQ ID NO 23
<211> LENGTH: 39
<212> TYPE: DNA
<213> ORGANISM: Artificial Sequence
<220> FEATURE:
<223> OTHER INFORMATION: Oligo d(T)-anchor primer

<400> SEQUENCE: 23
gaccacgcgt atcgatgtcg acttttttttt tttttttv                            39

<210> SEQ ID NO 24
<211> LENGTH: 22
<212> TYPE: DNA
<213> ORGANISM: Artificial Sequence
<220> FEATURE:
<223> OTHER INFORMATION: PCR anchor primer

<400> SEQUENCE: 24
gaccacgcgt atcgatgtcg ac                                              22

<210> SEQ ID NO 25
<211> LENGTH: 29
<212> TYPE: DNA
<213> ORGANISM: Artificial Sequence
<220> FEATURE:
<223> OTHER INFORMATION: CVGI169 primer

```
<400> SEQUENCE: 25
ttgggtaacg ccagggtttt cccagtcac                                29

<210> SEQ ID NO 26
<211> LENGTH: 29
<212> TYPE: DNA
<213> ORGANISM: Artificial Sequence
<220> FEATURE:
<223> OTHER INFORMATION: CVGI170 primer

<400> SEQUENCE: 26
ccccaggctt tacactttat gcttccggc                                29

<210> SEQ ID NO 27
<211> LENGTH: 20
<212> TYPE: DNA
<213> ORGANISM: Artificial Sequence
<220> FEATURE:
<223> OTHER INFORMATION: CVGI171 primer

<400> SEQUENCE: 27
gccagtacag ccctgatgat                                          20

<210> SEQ ID NO 28
<211> LENGTH: 22
<212> TYPE: DNA
<213> ORGANISM: Artificial Sequence
<220> FEATURE:
<223> OTHER INFORMATION: CVGI172 primer

<400> SEQUENCE: 28
tccccagtgt ctgaagtgga tg                                       22

<210> SEQ ID NO 29
<211> LENGTH: 22
<212> TYPE: DNA
<213> ORGANISM: Artificial Sequence
<220> FEATURE:
<223> OTHER INFORMATION: CVGI281 primer

<400> SEQUENCE: 29
ctcattcgct acatgcatac ct                                       22

<210> SEQ ID NO 30
<211> LENGTH: 22
<212> TYPE: DNA
<213> ORGANISM: Artificial Sequence
<220> FEATURE:
<223> OTHER INFORMATION: CVGI282 primer

<400> SEQUENCE: 30
cggccttgtg tcaaggtgga tg                                       22

<210> SEQ ID NO 31
<211> LENGTH: 22
<212> TYPE: DNA
<213> ORGANISM: Artificial Sequence
<220> FEATURE:
<223> OTHER INFORMATION: CVGI283 primer

<400> SEQUENCE: 31
cttctggact gagttctcca tc                                       22

<210> SEQ ID NO 32
```

```
<211> LENGTH: 22
<212> TYPE: DNA
<213> ORGANISM: Artificial Sequence
<220> FEATURE:
<223> OTHER INFORMATION: CVGI390 primer

<400> SEQUENCE: 32
caggagactg aatccagagc tg                                          22

<210> SEQ ID NO 33
<211> LENGTH: 22
<212> TYPE: DNA
<213> ORGANISM: Artificial Sequence
<220> FEATURE:
<223> OTHER INFORMATION: CVGI391 primer

<400> SEQUENCE: 33
gacagtagtc aaggccagca gc                                          22

<210> SEQ ID NO 34
<211> LENGTH: 22
<212> TYPE: DNA
<213> ORGANISM: Artificial Sequence
<220> FEATURE:
<223> OTHER INFORMATION: CVGI457 primer

<400> SEQUENCE: 34
gagaccatga ctactgccag gt                                          22

<210> SEQ ID NO 35
<211> LENGTH: 22
<212> TYPE: DNA
<213> ORGANISM: Artificial Sequence
<220> FEATURE:
<223> OTHER INFORMATION: CVGI458 primer

<400> SEQUENCE: 35
accgctctgg aggaggaaga ct                                          22

<210> SEQ ID NO 36
<211> LENGTH: 22
<212> TYPE: DNA
<213> ORGANISM: Artificial Sequence
<220> FEATURE:
<223> OTHER INFORMATION: CVGI535 primer

<400> SEQUENCE: 36
ttaagcctta accctttgag ga                                          22

<210> SEQ ID NO 37
<211> LENGTH: 22
<212> TYPE: DNA
<213> ORGANISM: Artificial Sequence
<220> FEATURE:
<223> OTHER INFORMATION: CVGI536

<400> SEQUENCE: 37
ggcccagata caccgactat ga                                          22

<210> SEQ ID NO 38
<211> LENGTH: 20
<212> TYPE: DNA
<213> ORGANISM: Artificial Sequence
<220> FEATURE:
<223> OTHER INFORMATION: PGC-3 forward primer

<400> SEQUENCE: 38
```

-continued

```
tgctggccca gatacactga                                    20

<210> SEQ ID NO 39
<211> LENGTH: 21
<212> TYPE: DNA
<213> ORGANISM: Artificial Sequence
<220> FEATURE:
<223> OTHER INFORMATION: PGC-3 reverse primer

<400> SEQUENCE: 39
ggctgttatc aatgcaggct c                                  21

<210> SEQ ID NO 40
<211> LENGTH: 28
<212> TYPE: DNA
<213> ORGANISM: Artificial Sequence
<220> FEATURE:
<223> OTHER INFORMATION: PGC-3 probe

<400> SEQUENCE: 40
cgtcagggaa aagcaagtat gaagccat                           28
```